United States Patent
Fritz et al.

(10) Patent No.: US 10,499,816 B2
(45) Date of Patent: Dec. 10, 2019

(54) CSF SHUNT FLOW EVALUATION APPARATUS AND METHOD USING A CONFORMABLE EXPANDED DYNAMIC RANGE THERMOSENSOR

(71) Applicants: SHUNTCHECK, INC., Princeton, NJ (US); Frederick J. Fritz, Skillman, NJ (US); Marek Swoboda, Philadelphia, PA (US); Mark E. Mattiucci, Newton Square, PA (US); Matias G. Hochman, Philadelphia, PA (US)

(72) Inventors: Frederick J. Fritz, Skillman, NJ (US); Marek Swoboda, Philadelphia, PA (US); Mark E. Mattiucci, Newton Square, PA (US); Matias G. Hochman, Philadelphia, PA (US)

(73) Assignee: ShuntCheck, Inc., Yardley, PA (US)

(*) Notice: Subject to any disclaimer, the term of this patent is extended or adjusted under 35 U.S.C. 154(b) by 97 days.

(21) Appl. No.: 14/648,358

(22) PCT Filed: Nov. 26, 2013

(86) PCT No.: PCT/US2013/071928
§ 371 (c)(1),
(2) Date: May 29, 2015

(87) PCT Pub. No.: WO2014/088886
PCT Pub. Date: Jun. 12, 2014

(65) Prior Publication Data
US 2015/0305629 A1 Oct. 29, 2015

Related U.S. Application Data

(60) Provisional application No. 61/797,389, filed on Dec. 6, 2012, provisional application No. 61/960,026, filed on Sep. 9, 2013.

(51) Int. Cl.
*A61B 5/01* (2006.01)
*A61M 27/00* (2006.01)

(52) U.S. Cl.
CPC ............. *A61B 5/01* (2013.01); *A61M 27/006* (2013.01)

(58) Field of Classification Search
None
See application file for complete search history.

(56) References Cited

U.S. PATENT DOCUMENTS

| 4,548,516 A | 10/1985 | Helenowski |
| 5,156,316 A * | 10/1992 | Nied ............... B23K 20/12 228/102 |

(Continued)

FOREIGN PATENT DOCUMENTS

| JP | 07-275210 | 10/1995 |
| JP | 10-276993 | 10/1998 |

(Continued)

OTHER PUBLICATIONS

Myron L. Cohen, Measurement of the Thermal Properties of Human Skin. A Review, 1977, vol. 69, No. 3, pp. 333-338.*

(Continued)

*Primary Examiner* — Devin B Henson
*Assistant Examiner* — Benjamin S Melhus
(74) *Attorney, Agent, or Firm* — Caesar Rivise, PC

(57) ABSTRACT

An apparatus and method that utilizes thermal dilution to detect a wide range of flow rates and/or flow status in cerebrospinal fluid (CSF) shunt systems. The use of a large cold source in combination with thermosensor pad of a particular construction provide a fluid flow analyzer with the ability to detect very low levels of CSF flow. In addition, a method for adjusting thermal dilution readings to compensate for varying shunt catheter depth is shown and for (Continued)

determining a steady state of the thermal dilution readings. The thermosensor pad is conformable to a patient's skin contour thereby making the apparatus and method less sensitive to ambient temperature errors and, as a result, more accurate in assessing CSF flow. Furthermore, a software error check is provided for identifying poor sensor-to-skin contact for alerting an operator to re-apply the thermosensor pad to correct, as well as a post-test check to determine if temperature data is reasonable before determining flow status or flow rate.

21 Claims, 17 Drawing Sheets

(56) References Cited

U.S. PATENT DOCUMENTS

| | | | |
|---|---|---|---|
| 5,255,979 | A | 10/1993 | Ferrari |
| 5,579,778 | A * | 12/1996 | Baker ............... A61B 5/7267 128/925 |
| 7,520,862 | B2 | 4/2009 | Neff |
| 7,625,117 | B2 | 12/2009 | Haslett et al. |
| 8,075,470 | B2 | 12/2011 | Alekseyenko et al. |
| 8,302,471 | B2 | 11/2012 | Van Der Wiel |
| 8,551,011 | B2 | 10/2013 | Fritz et al. |
| 8,894,584 | B2 | 11/2014 | Swoboda et al. |
| 2002/0035340 | A1 | 3/2002 | Fraden et al. |
| 2002/0121137 | A1 | 9/2002 | Fujiwara et al. |
| 2003/0004495 | A1 | 1/2003 | Saul |
| 2004/0068201 | A1 | 4/2004 | Saul |
| 2004/0147871 | A1 | 7/2004 | Burnett |
| 2004/0230117 | A1 * | 11/2004 | Tosaya ............. A61B 17/22004 600/439 |
| 2005/0094707 | A1 | 5/2005 | Lee et al. |
| 2005/0149170 | A1 | 7/2005 | Tassel et al. |
| 2005/0171452 | A1 | 8/2005 | Neff |
| 2005/0204811 | A1 | 9/2005 | Neff |
| 2006/0000271 | A1 | 1/2006 | Bork |
| 2006/0235349 | A1 | 10/2006 | Osborn et al. |
| 2007/0073132 | A1 | 3/2007 | Vosch |
| 2007/0106172 | A1 | 5/2007 | Abreau |
| 2007/0206655 | A1 | 9/2007 | Haslett et al. |
| 2007/0282218 | A1 | 12/2007 | Yarden |
| 2008/0039739 | A1 | 2/2008 | Buja |
| 2008/0077201 | A1 * | 3/2008 | Levinson ............... A61B 5/411 607/96 |
| 2008/0150682 | A1 | 6/2008 | Shii |
| 2008/0207984 | A1 | 8/2008 | Alekseyenko et al. |
| 2008/0214951 | A1 | 9/2008 | Fritz et al. |
| 2009/0164163 | A1 | 6/2009 | Wang et al. |
| 2009/0326410 | A1 * | 12/2009 | James ............... A61B 10/0012 600/551 |
| 2010/0022903 | A1 * | 1/2010 | Sitzman ............. A61B 5/04017 600/509 |
| 2010/0228179 | A1 | 9/2010 | Thomas |
| 2011/0054382 | A1 | 3/2011 | Fritz |
| 2012/0029310 | A1 * | 2/2012 | Paquet ............... A61B 5/0008 600/301 |
| 2012/0083673 | A1 * | 4/2012 | Al-Ali ............... A61B 5/0006 600/301 |
| 2012/0245661 | A1 | 9/2012 | Mason |
| 2012/0289855 | A1 * | 11/2012 | Bieberich ............. G01K 1/165 600/549 |

FOREIGN PATENT DOCUMENTS

| | | |
|---|---|---|
| JP | 2004-513681 A | 5/2004 |
| JP | 2006-017722 | 1/2006 |
| JP | 2008-032544 | 2/2008 |
| JP | 2009-189815 | 8/2009 |
| WO | WO 02/07596 | 7/2002 |
| WO | WO 2008-127867 | 10/2008 |
| WO | WO 2009-146075 | 12/2009 |
| WO | WO 2011-150323 | 12/2011 |

OTHER PUBLICATIONS

Arthur E. Marlin, Sarah J. Gaskill; The Use of Transcutaneous Thermal Convection Analysis to Assess Shunt Function in the Pediatric Population, Operative Neurosurgery, vol. 70, Issue suppl_2, Jun. 1, 2012, pp. ons181-ons183, https://doi.org/10.1227/NEU.0b013e31823cf18d.*

Goetz, C., Foertsch, D., Schoenberger, J. et al.; Thermography—a valuable tool to test hydrocephalus shunt patency; Acta Neurochir (Wien) (2005) 147: 1167. https://doi.org/10.1007/s00701-005-0608-1.*

International Search Report for related PCT Application No. PCT/US2011/037218 dated Jan. 10, 2012.

International Search Report for related PCT Application No. PCT/US2011/038317 dated Feb. 24, 2012.

International Search Report for related PCT Application No. PCT/US2013/052018 dated Nov. 6, 2013.

International Search Report for related PCT Application No. PCT/US2009/039146 dated Oct. 1, 2009.

Bech-Azeddine, et al., "Idiopathic Normal-Pressure Hydrocephalus: Clinical Comorbidity Corrected With Cerebrospinal With Cerebral Biopsy Findings and Outcome of Cerebrospinal Fluid Shunting", Journal of Neurology, Neurosurgery & Psychiatry, vol. 78, pp. 157-161, 2007.

Cohen, M., "Measurement of the Thermal Properties of Human Skin. A Review", The Journal of Investigative Dermatology, vol. 69, No. 3, pp. 333-338, 1977.

Drake J., et al., "Cerebrospinal Fluid Flow Dynamics in Children with External Ventricular Drains", Neurosurgery, vol. 28, No. 2, pp. 242-250, 1991.

Drake, J., et al., "Randomized Trial of Cerebrospinal Fluid Shunt Calve Design in Pediatric Hydrocephalus", Neurosurgery, vol. 43, Issue 2, pp. 1-39, Aug. 1998.

Eggleston, T., et al., "Comparison of Two Porcine (Sus scrofa domestica) Skin Models for In Vivo Near-Infrared Laser Exposure", Comparative Medicine, vol. 50, No. 4, pp. 391-397, Aug. 2000.

Hidaka M., et al., "Dynamic Measurement of the Flow Rate in Cerebrospinal Fluid Shunts in Hydrocephalic Patients", European Journal of Nuclear Medicine, vol. 28, No. 7, pp. 888-893, Jul. 2001.

Iskandar, B., et al., "Death in Shunted Hydrocephalic Children in the 1990s", Pediatric Neurosurgery, vol. 28, pp. 173-176, Apr. 1998.

Iskandar, B., et al., "Pitfalls in the Diagnosis of Ventricular Shunt Dysfunction: Radiology Reports and Ventricular Size", Pediatrics, vol. 101, No. 6, pp. 1031-1036, Jun. 1998.

Kestle, J., et al., "Lack of Benefit of Endoscopic Ventriculoperitoneal Shunt Insertion: A Multicenter Randomized Trial", Journal of Neurosurgery, vol. 98, pp. 284-290, Feb. 2003.

Laurence, K., et al., "The Natural History of Hydrocephalus", Archives of Disease in Childhood, pp. 345-362, Apr. 1962.

McGirt, M., et al., "Cerebropsinal Shunt Survival and Etiology of Failures: A Seven-Year Institutional Experience", Pediatric Neurosurgery, vol. 36, No. 5, pp. 248-255, May 2002.

Patwardhan, N., et al., "Implanted Ventricular Shunts in the United States: The Billion Dollar a Year Cost of Hydrocephalus Treatment", Neurosurgery, vol. 56, No. 1, pp. 139-145, Jan. 2005.

Piatt, J., "Physical Examination of Patients with Cerebrospinal Fluid Shunts: Is There Useful Information in Pumping the Shunt?", Pediatrics, vol. 89, pp. 470-473, Mar. 1992.

Pitteti, R., "Emergency Department Evaluation of Ventricular Shunt Malfunction: Is the Shunt Series Really Necessary?", Pediatric Emergency Care, vol. 23, No. 3, pp. 137-141, Mar. 2007.

Sood S., et al., "Evaluation of Shunt Malfunction Using Shunt Site Reservoir", Pediatric Neurosurgery, vol. 32, pp. 180-186, 2000.

Ventureyra, E., et al., "A New Ventricular Catheter for the Prevention and Treatment of Proximal Obstruction in Cerebrospinal Fluid Shunts", Neurosurgery, Issue 34(5), pp. 924-926, May 1994.

Stein, et al., "A Noninvasive Approach to Quantitive Measurement of Flow Through CSF Shunts," J. Neurosurg., vol. 54, Apr. 1981.

(56) References Cited

OTHER PUBLICATIONS

Zorc, J., et al., "Radiographic Evaluation for Suspected Cerebrospinal Fluid Shunt Obstruction", Pediatric Emergency Care, vol. 18, No. 5, pp. 337-340, 2002.
International Search Report for PCT/US2013/071928 dated Mar. 6, 2014.

* cited by examiner

CSF SHUNT FLOW EVALUATION APPARATUS AND METHOD USING A CONFORMABLE EXPANDED DYNAMIC RANGE THERMOSENSOR

CROSS-REFERENCE TO RELATED APPLICATIONS

This U.S. national phase application claims the benefit under 35 U.S.C. § 371 of PCT application no. PCT/US2013/071928 filed on Nov. 26, 2013 entitled CSF SHUNT FLOW EVALUATION APPARATUS AND METHOD USING A CONFORMABLE EXPANDED DYNAMIC RANGE THERMOSENSOR which in turn claims the benefit under 35 U.S.C. § 119(e) of Provisional Application Ser. No. 61/797,389 filed on Dec. 6, 2012 entitled EXPANDED DYNAMIC RANGE CSF SHUNT FLOW THERMOSENSOR AND TEST PACK and also claims the benefit under 35 U.S.C. § 119(e) of Provisional Application Ser. No. 61/960,026 filed on Sep. 9, 2013 entitled CONFORMABLE EXPANDED DYNAMIC RANGE CSF SHUNT FLOW THERMOSENSOR and all of whose entire disclosures are incorporated by reference herein.

STATEMENT REGARDING FEDERALLY SPONSORED RESEARCH OR DEVELOPMENT

This invention was made with government support under R44NS067772 awarded by the National Institutes of Health. The government has certain rights in the invention.

BACKGROUND OF THE INVENTION

1. Field of Invention

This present invention generally relates to cerebrospinal fluid (CSF) shunts and, more particular, to a device and method for testing for the presence, absence and/or rate of CSF flow through shunt tubing implanted under the skin in hydrocephalus patients.

2. Description of Related Art

Hydrocephalus is a condition of abnormal cerebrospinal fluid (CSF) homeostasis, resulting in an accumulation of CSF in the brain ventricles. Approximately 69,000 people are diagnosed with hydrocephalus each year in the United States, most commonly as a congenital condition, making it one of the most common birth defects. Untreated hydrocephalus leads to progressive neurological dysfunction and death.

The most commonly used treatment for hydrocephalus is diversion of CSF from the ventricles to the peritoneal cavity by means of a permanent prosthetic shunt. A CSF shunt is comprised of a valve connected to a tube. The proximal end of the tube is surgically inserted into the ventricle of the brain, and runs subcutaneously through the body into the abdominal cavity (FIG. 1). There are approximately 300,000 shunted hydrocephalus patients in the US. 41,000 shunt procedures are performed each year, approximately 12,000 of which are new shunt placements.

Improved materials, diagnostic, and treatment technologies, have improved shunt therapy since the 1970s. However, shunt failure is still almost inevitable during a patient's life. The one-year failure rate of ventriculoperitoneal shunts has been estimated to be approximately 40%, and the mean period to failure of an implanted shunt is typically only 5-10 years. Obstruction of the ventricular catheter, usually from tissue ingrowth or clots, is overwhelmingly the greatest cause of shunt failure. Shunt failure can rapidly progress to life-threatening elevation in intracranial pressure, so revision surgery, and re-placement of the blocked ventricular catheter is indicated. More than half of all shunt procedures in the United States are revisions.

However, since catheter replacement surgery carries risks of life-threatening complications such as infection or embolism, a need for shunt revision needs to be reasonably established. The problem is that the usual clinical manifestations of shunt failure, such as headaches, vomiting, or loss of vision, are non specific and are difficult to differentiate from common, less serious illnesses, particularly in pediatric patients. This leads to two extremes of management: patient families who present persistently at emergency rooms for every headache or flu symptom, and patient families who dangerously dismiss symptoms of a shunt blockage as a common ailment. A study at the Children's Hospital of Philadelphia (CHOP) indicates that they see three false alarms for every true shunt malfunction. There is a need for objective methods to evaluate suspected shunt obstruction.

An unacceptably high number of hydrocephalic children still die as a result of shunt malfunction, primarily because of a failure to identify shunt blockage at an early stage. The early diagnosis of shunt obstruction is complex and difficult. While a number of shunt flow detection methods are available, none are diagnostic when used alone or are without complication, and there is little standardization to guide physicians in their interpretation (Table 1). Physical examination of the patient, including pumping of the shunt reservoir, is unreliable. Measuring CSF pressure by "shunt tap" is invasive, painful, and can be misleading. CT and MR, either alone, or in combination with plain radiographs, remain the gold standards for diagnosis of shunt malfunction. However, these imaging techniques are static, and so must be performed multiple times to detect ventricular enlargement. This results in repeated radiological exposures of patients (often children), a safety concern for pediatric neurosurgeons. Furthermore, the reliability of these techniques for detecting CSF accumulation has been questioned. For a while, radionuclide markers were widely used to derive truly dynamic information about CSF flow in the brain and in shunts. However, their promise was never wholly realized, and they are not routinely utilized in most clinical settings. Because of the expense and technical complexity of advanced imaging techniques, they cannot be used to investigate every headache.

TABLE 1

Table 1: Performance of Commonly-Used Diagnostic Procedures for Suspected CSF Shunt Obstruction

| Diagnostic Procedure | Sensitivity (Detecting No Flow) | Specificity (Detecting Flow) | Features |
|---|---|---|---|
| Static Imaging Procedures | | | |
| CT Scan [36] | 68% | 90% | Expensive, time-consuming, radiation dose. Shunt malfunction must have gone on long enough for the scan to detect visible changes, i.e. ventricle enlargement. Rising concern about radiation. |

TABLE 1-continued

Table 1: Performance of Commonly-Used Diagnostic Procedures for Suspected CSF Shunt Obstruction

| Diagnostic Procedure | Sensitivity (Detecting No Flow) | Specificity (Detecting Flow) | Features |
| --- | --- | --- | --- |
| X-ray Series [36] | 27% | 99% | Expensive and time-consuming. As with CT, the shunt must have malfunctioned long enough for visible changes to be detected. |
| Dynamic Flow Measurements | | | |
| Shunt Tap [37] | 79% | 56% | Method is painful, risks infection and can be inconclusive if blockage is upstream of the tap area. |
| Radio Isotope [38] | 80% | 53% | Requires an invasive shunt tap and 24 hours lead time for isotope. This method is considerably more involved than either the CT or MRI. |

The current, non-invasive imaging procedures have relatively low sensitivity and better specificity—making them reasonable rule-in tests but poor rule-out tests. The invasive procedures are somewhat better rule-out tests, but are painful and present an infection risk. Furthermore, children are often sent to CT Scans, the most commonly used procedures, when they present to the ER and such repeat exposure to radiation may be harmful. What is needed is a simple and reliable method for determining CSF shunt flow rates that can be interpreted by neurosurgeons and non-neurosurgeons with equal confidence.

To meet the need for rapid and sensitive methods for determining shunt function, Applicant has developed a method to allow non-invasive detection of cerebrospinal fluid flow through subcutaneous shunts under the rubric "ShuntCheck." ShuntCheck involves devices using thermal dilution technology—detecting a transcutaneous change in temperature as cooled cerebrospinal fluid flows through the subcutaneous portion of a ventriculoperitoneal shunt. See U.S. Patent Application No. 2013/0109998 (which is incorporated by reference in its entirety herein), owned by the same Applicant as the present application, namely, ShuntCheck, Inc. As shown most clearly in FIG. 2A, one early version 10 of ShuntCheck, namely, "ShuntCheck v2.2", comprises a single use disposable thermosensor 12 which is placed on the skin 11 over a subcutaneous shunt 13; a personal digital assistant (PDA)-based BioDisplay 14 which includes an A/D converter for converting and conditioning the analog sensor signal into digital signal; this PDA-based BioDisplay includes ShuntCheck software which analyzes temperature data from the thermosensor and provides a time-temperature graph and a flow or no-flow result. Side 12A of the thermosensor 12 faces upward when placed against the skin 11 and side 12B (FIG. 2B) is adhesively secured to the skin 11, once a release strip 15 is removed. ShuntCheck also includes the "Micro-Pumper" (see FIGS. 2C and 2D), a device which generates a temporary increase in CSF flow in patent, but not in occluded CSF, shunts. See U.S. Patent Publication No. 2013/0102951, also owned by ShuntCheck, Inc. and which is also incorporated by reference in its entirety herein.

As shown in FIG. 2D, the Micro-Pumper 300 is hand-held device that is positioned against the skin 11 over the dome portion 210 of the CSF shunt's valve 211; the valve 211 is typically implanted over bone 220 of the patient's skull. A foot 301 having short rods 302 is reciprocated against the dome 210 by a Micro-Pumper drive system (FIG. 2C) including a shaft 306, a spring 305, a piston 304 and a cam 307 driven by a motor (not shown).

As shown in FIG. 2B, the thermosensor 12 comprises a plurality of temperature sensors TS (e.g., thermistors, e.g., GE thermistors, by way of example only) and is adhesively placed on the skin 11 where the shunt 13 crosses the clavicle. Ice 17 (or, e.g., ice within a receptacle) is placed on the skin, "upstream" of the CSF flow (viz., in window 19) from the plurality of temperature sensors 17, to cool the CSF in the shunt 11. Temperature sensors TS placed over the shunt 13 detect the change in temperature as cooled fluid flows beneath them. The presence of flowing fluid is interpreted as a decrease in temperature detected by the temperature sensors TS, while no change in temperature indicates the absence of flow. The ShuntCheck method/devices can assess the rate of CSF fluid flow through shunts. The temperature drop recorded by ShuntCheck method/devices varies linearly with flow rate-the deeper the temperature drop, the faster the flow (see FIG. 3).

Further testing of the thermosensor 12 determined that intermittent CSF flow is likely to be a limiting factor on specificity performance of any method in which shunt patency or obstruction is being inferred from fluid flow measurements. As a result, the Micro Pumper was developed. As discuss previously, the Micro Pumper 300 is a miniature, non-invasive device which is held against the shunt valve (which is typically implanted under the scalp behind the ear) and which provides a specific vibration pulse to the valve. The vibration pulses act like a manual shunt pumping in miniature and generate a temporary increase in shunt flow through patent, but not through occluded shunts. However, in certain instances flows enhanced by use of the Micro Pumper 300 resulted in flows beyond the detection of the ShuntCheck v 2.2 device.

Thus, there remains a need for an improved thermosensor design and a new method for providing thermal dilution cooling which permits the non-invasive detection of cerebrospinal fluid flow through subcutaneous shunts.

All references cited herein are incorporated herein by reference in their entireties.

BRIEF SUMMARY OF THE INVENTION

A sensor pad is disclosed which is adapted for releasable application to the skin of a patient having a subcutaneous cerebrospinal fluid (CSF) shunt having CSF that flows from an upstream location in the patient towards a downstream location and also wherein the sensor pad is also adapted for use with a cerebrospinal fluid (CSF) analyzer. The sensor pad comprises: a body (e.g., an EVA foam) comprising a plurality of temperature sensors (e.g., NTC thermistors) that are positioned transversely across the body at predetermined positions, wherein the plurality of temperature sensors are aligned such that when the sensor pad is applied to the skin over the CSF shunt, one of the plurality of temperature sensors is positioned over the CSF shunt while the remaining plurality of temperature sensors are equally positioned on opposite sides of the CSF shunt; the body further comprises an alignment member that protrudes from an edge of the pad, wherein the alignment member acts as a guide for a user in positioning a cold source (e.g., an instant ice pack, 3"×3" or larger) against the skin of the patient to maintain the cold source at a predetermined upstream position (e.g., between 16 mm and 36 mm, preferably 28 mm) away from the plurality of temperature sensors over the CSF shunt, and wherein the sensor pad is disposable.

An apparatus is disclosed for evaluating cerebrospinal fluid (CSF) flow rate or flow status in a CSF shunt within a patient. The apparatus comprises: a sensor pad having a body (e.g., an EVA foam) comprising a plurality of temperature sensors (e.g., NTC thermistors) that are positioned transversely across the body at predetermined positions, wherein the plurality of temperature sensors are aligned such that when the sensor pad is applied to the skin over the CSF shunt, one of the plurality of temperature sensors is positioned over the CSF shunt while the remaining plurality of temperature sensors are equally positioned on opposite sides of the CSF shunt; each of the temperature sensors is configured to generate respective temperature data related to movement of a temperature pulse introduced into the CSF from a cold source (e.g., an instant ice pack, 3"×3" or larger) applied to the skin for a predetermined period; the body further comprises an alignment member that protrudes from an edge of the pad, wherein the alignment member acts as a guide for a user in positioning the cold source against the skin of the patient to maintain the cold source at a predetermined upstream position (e.g., between 16 mm and 36 mm, preferably 28 mm) away from the plurality of temperature sensors over the CSF shunt, and wherein the sensor pad is disposable; and a sensor processing device that is electrically coupled to the sensor pad for receiving temperature data from each of the temperature sensors, wherein the sensor processing device uses the temperature data to determine a flow rate or flow status of the CSF through the shunt when the cold source is applied at the predetermined upstream position.

A method for evaluating cerebrospinal fluid (CSF) flow rate or flow status in a subcutaneous CSF shunt is disclosed. The method comprises: applying a disposable pad having a body (e.g., an EVA foam) including a plurality of temperature sensors (e.g., NTC thermistors) that are positioned transversely across the body at predetermined positions, wherein the plurality of temperature sensors are aligned such that when the sensor pad is applied to the patient's skin over the CSF shunt, one of the plurality of temperature sensors is positioned over the CSF shunt while the remaining plurality of temperature sensors are equally positioned on opposite sides of the CSF shunt; applying a cold source (e.g., an instant ice pack, 3"×3" or larger) over the CSF shunt and upstream of the plurality of temperature sensors for a predetermined period, wherein the step of applying the cold source comprises positioning the cold source above an alignment member that protrudes from an edge of the pad for maintaining the cold source at a predetermined upstream position (e.g., between 16 mm and 36 mm, preferably 28 mm) away from the plurality of temperature sensors over the CSF shunt; collecting temperature data from the plurality of temperature sensors; generating a resultant temperature signal from the temperature data; and determining a flow rate or flow status of the CSF through the shunt from the resultant temperature signal.

An apparatus for measuring changes in skin temperature above a subcutaneous CSF shunt is also disclosed. The apparatus comprises: a sensor pad having a body (e.g., an EVA foam) comprising a plurality of temperature sensors that are positioned transversely across the body at predetermined positions, wherein the plurality of temperature sensors (e.g., NTC thermistors) are aligned such that when the sensor pad is applied to the skin over the CSF shunt, one of the plurality of temperature sensors is positioned over the CSF shunt while the remaining plurality of temperature sensors are equally positioned on opposite sides of the CSF shunt; each of the temperature sensors is configured to generate respective temperature data related to movement of a temperature pulse introduced into the CSF from a cold source (e.g., an instant ice pack, 3"×3" or larger) applied to the skin for a predetermined period; the body further comprises an alignment member that protrudes from an edge of the pad, wherein the alignment member acts as a guide for a user in positioning the cold source against the skin of the patient to maintain said cold source at a predetermined upstream position (e.g., between 16 mm and 36 mm, preferably 28 mm) away from the plurality of temperature sensors over the CSF shunt, and wherein the sensor pad is disposable; and a sensor processing device that is electrically coupled to the sensor pad for receiving temperature data from each of the temperature sensors, wherein the sensor processing device comprises an algorithm for taking the difference between the temperature data of the one of the plurality of temperature sensors that is positioned over the CSF shunt and an average of the temperature data of the remaining plurality of temperature sensors positioned on opposite sides of the CSF shunt, and wherein the algorithm adjusts the difference between the temperature data based on the location of the CSF shunt below the skin surface by multiplying the temperature difference by a ratio of actual skin thickness to average skin thickness.

A method for measuring changes in skin temperature above a subcutaneous CSF shunt is disclosed. The method comprises: applying a disposable pad having a body (e.g., an EVA foam) including a plurality of temperature sensors (e.g., NTC thermistors) that are positioned transversely across the body at predetermined positions, wherein the plurality of temperature sensors are aligned such that when the sensor pad is applied to the patient's skin over the CSF shunt, one of the plurality of temperature sensors is positioned over the CSF shunt while the remaining plurality of temperature sensors are equally positioned on opposite sides of the CSF shunt; applying a cold source (e.g., an instant ice pack, 3"×3" or larger) over the CSF shunt and upstream of the plurality of temperature sensors for a predetermined period, wherein the step of applying the cold source comprises positioning the cold source above an alignment member that protrudes from an edge of the pad for maintaining the cold source at a predetermined upstream position (e.g., between 16 mm and 36 mm, preferably 28 mm) away from the plurality of temperature sensors over the CSF shunt; collecting temperature data from the plurality of temperature sensors; generating a resultant temperature signal from the temperature data by taking a difference between the temperature data of the one of the plurality of temperature sensors that is positioned over the CSF shunt and an average of the temperature data of the remaining plurality of temperature sensors positioned on opposite sides of the CSF shunt; and correcting the temperature data based on the location of the CSF shunt below the skin surface by multiplying the temperature difference by a ratio of actual skin thickness to average skin thickness.

An apparatus for quantifying temperature sensor signal noise generated by poor contact of a plurality of temperature sensors applied to the skin of the patient is disclosed. The apparatus comprises: a sensor pad having a body (e.g., an EVA foam) comprising a plurality of temperature sensors (e.g., NTC thermistors) that are positioned transversely across the body at predetermined positions, wherein the plurality of temperature sensors are aligned such that when the sensor pad is applied to the skin over the CSF shunt, one of the plurality of temperature sensors is positioned over the CSF shunt while the remaining plurality of temperature sensors are equally positioned on opposite sides of the CSF shunt; each of the temperature sensors is configured to generate respective temperature data related to movement of a temperature pulse introduced into the CSF from a cold source (e.g., an instant ice pack, 3"×3" or larger) applied to the skin for a predetermined period; the body further comprises an alignment member that protrudes from an edge of the pad, wherein the alignment member acts as a guide for a user in positioning the cold source against the skin of the patient to maintain the cold source at a predetermined upstream position (e.g., between 16 mm and 36 mm, preferably 28 mm) away from the plurality of temperature sensors over the CSF shunt, and wherein the sensor pad is disposable; and a sensor processing device that is electrically coupled to the sensor pad for receiving temperature data from each of the temperature sensors, wherein the sensor processing device comprises an algorithm for quantifying signal noise generated by poor contact of the sensor pad to the skin of the patient, and wherein the algorithm comprises: measuring each rise and fall in temperature detected by each one of the plurality of sensors; converting each fall in temperature, comprising a negative number, into a positive number for each one of the plurality of sensors; totaling all temperature changes for each one of plurality of sensors to form a total error for each sensor; and comparing the total error of each sensor to a predetermined threshold to determine if the total error exceeds the predetermined threshold or not and re-applying the sensor pad to the skin and obtaining a new set of temperature data for all of the plurality of temperature sensors with the cold source applied if the predetermined threshold is exceeded.

A method for quantifying temperature sensor signal noise generated by poor contact of a plurality of temperature sensors applied to the skin of the patient is disclosed. The method comprises: applying a disposable pad having a body (e.g., an EVA foam) including a plurality of temperature sensors (e.g., NTC thermistors) that are positioned transversely across the body at predetermined positions, wherein the plurality of temperature sensors is aligned such that when the sensor pad is applied to the patient's skin over the CSF shunt, one of the plurality of temperature sensors is positioned over the CSF shunt while the remaining plurality of temperature sensors are equally positioned on opposite sides of the CSF shunt; applying a cold source (e.g., an instant ice pack, 3"×3" or larger) over the CSF shunt and upstream of the plurality of temperature sensors for a predetermined period, wherein the step of applying the cold source comprises positioning the cold source above an alignment member that protrudes from an edge of the pad for maintaining the cold source at a predetermined upstream position (e.g., between 16 mm and 36 mm, preferably 28 mm) away from the plurality of temperature sensors over the CSF shunt; collecting temperature data from the plurality of temperature sensors; and quantifying signal noise generated by poor contact of the sensor pad to the skin of the patient, wherein the step for quantifying comprises: measuring each rise and fall in temperature detected by each one of the plurality of sensors; converting each fall in temperature, comprising a negative number, into a positive number for each one of the plurality of sensors; totaling all temperature changes for each one of the plurality of sensors to form a total error for each sensor; and comparing the total error of each sensor to a predetermined threshold to determine if the total error exceeds the predetermined threshold or not and re-applying the sensor pad to the skin and obtaining a new set of temperature data for all of the plurality of temperature sensors with the cold source applied if the predetermined threshold is exceeded.

BRIEF DESCRIPTION OF SEVERAL VIEWS OF THE DRAWINGS

The invention will be described in conjunction with the following drawings in which like reference numerals designate like elements and wherein.

DETAILED DESCRIPTION OF THE INVENTION

Figure 1:
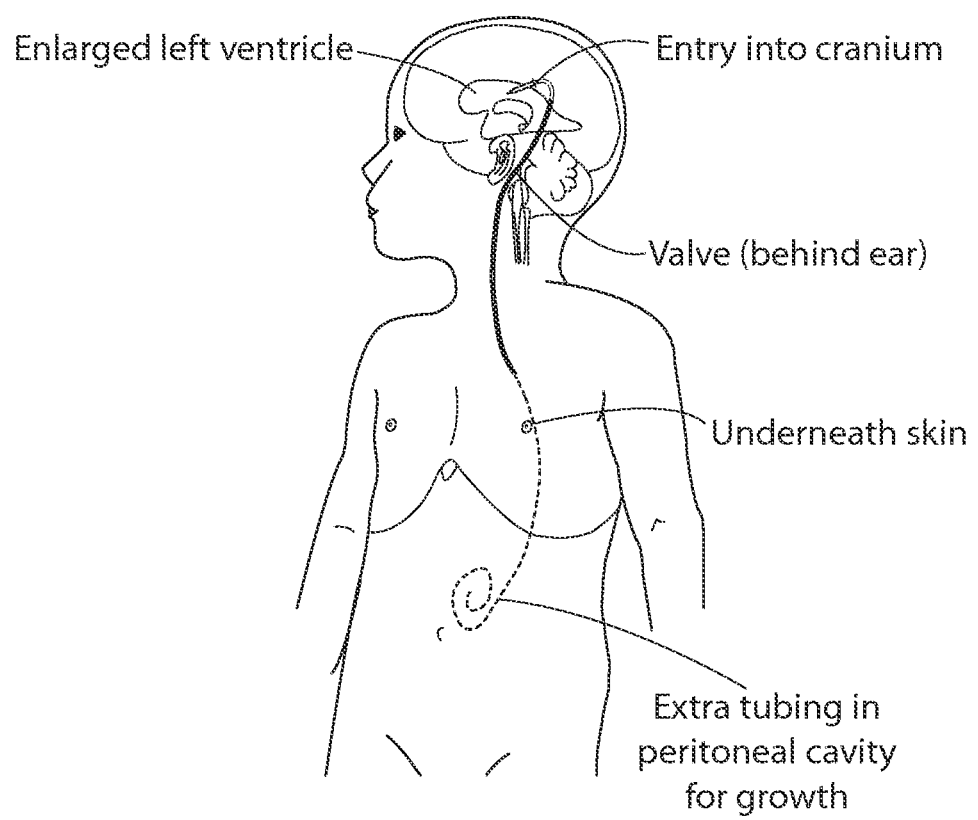
FIG. 1 is an illustration showing the anatomy of a typical CSF ventriculoperitoneal (VP) shunt.
Figure 2A:
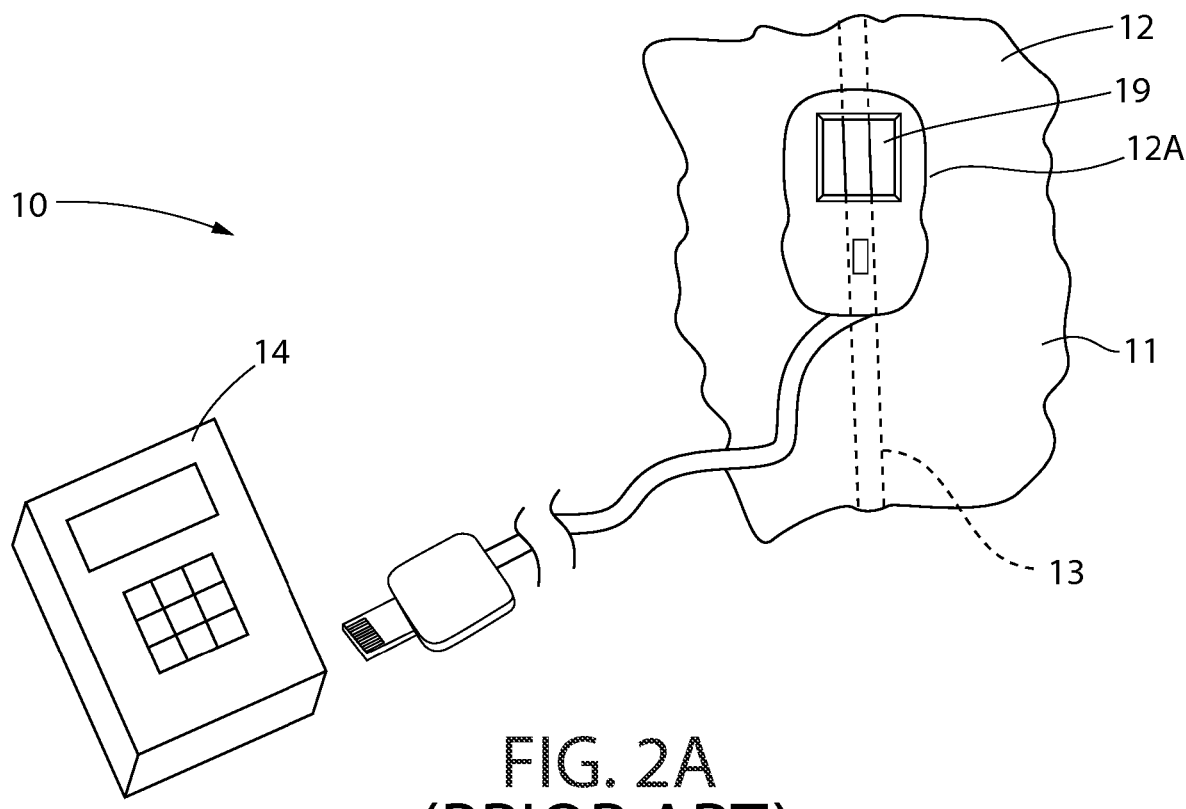
FIG. 2A shows the ShuntCheck v2.2 device having a thermosensor which is placed upon the skin of a patient over a CSF shunt, shown in phantom, with a cold source (e.g., an ice cube) placed within a thermosensor window and wherein the thermosensor is about to be coupled to a PDA-based BioDisplay unit for analyzing the collected temperature data and/or for relaying to a remote analyzer.
Figure 2B:
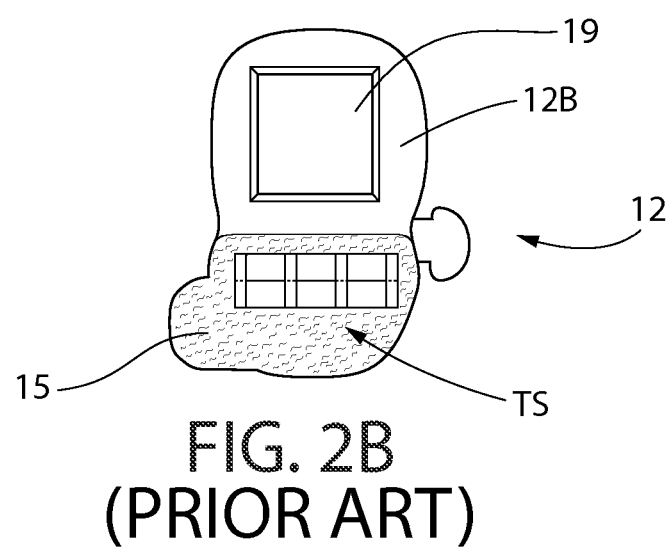
FIG. 2B shows the ShuntCheck v2.2 thermosensor from its back side which is adhesively coupled to the skin of the patient.
Figure 2C:
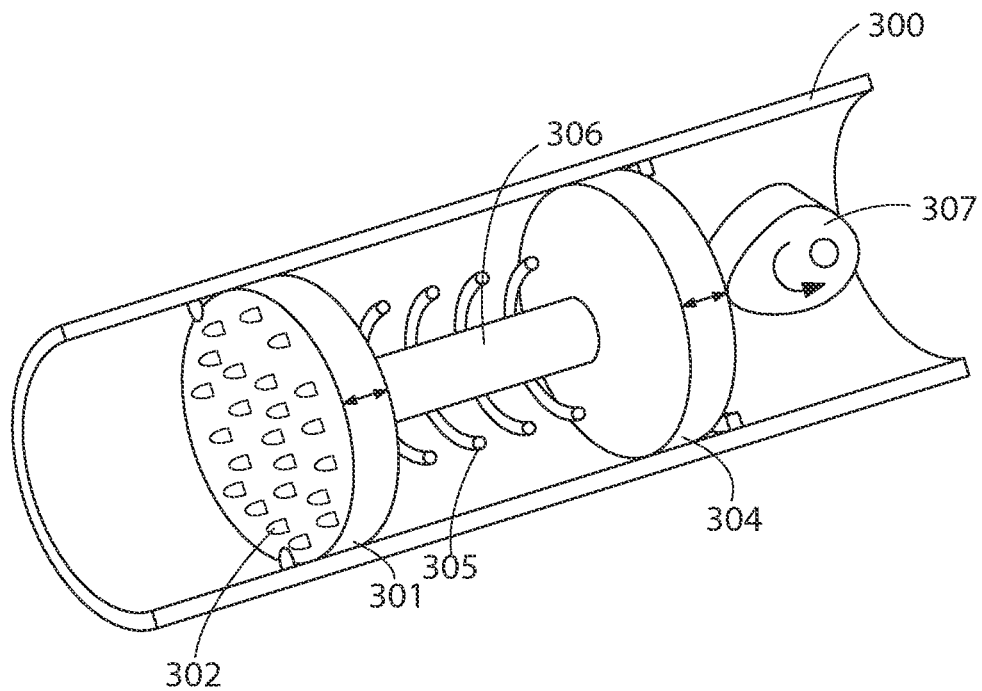
FIG. 2C is an enlarged isometric view, shown partially, of a prior art ShuntCheck micro-pumper device.
Figure 2D:
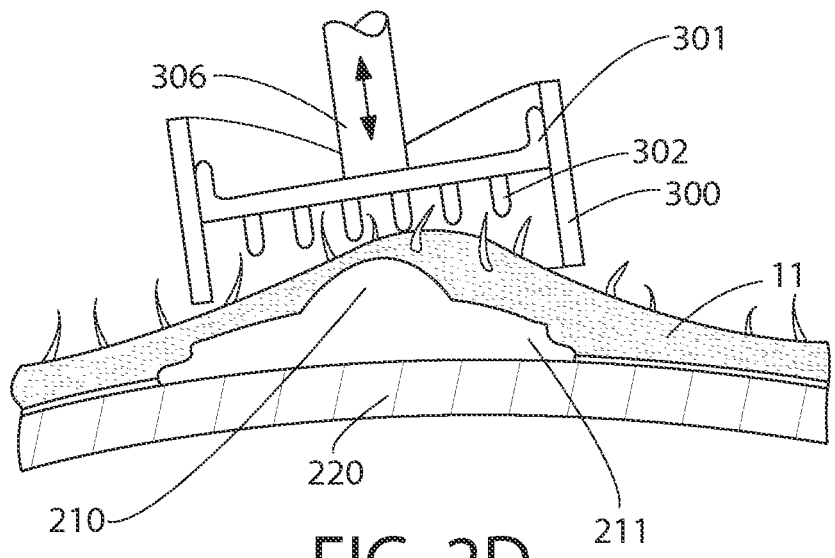
FIG. 2D is a sectional view of a portion of the micro-pumper of FIG. 2C placed on the scalp of the patient over the CSF shunt valve dome.
Figure 3:
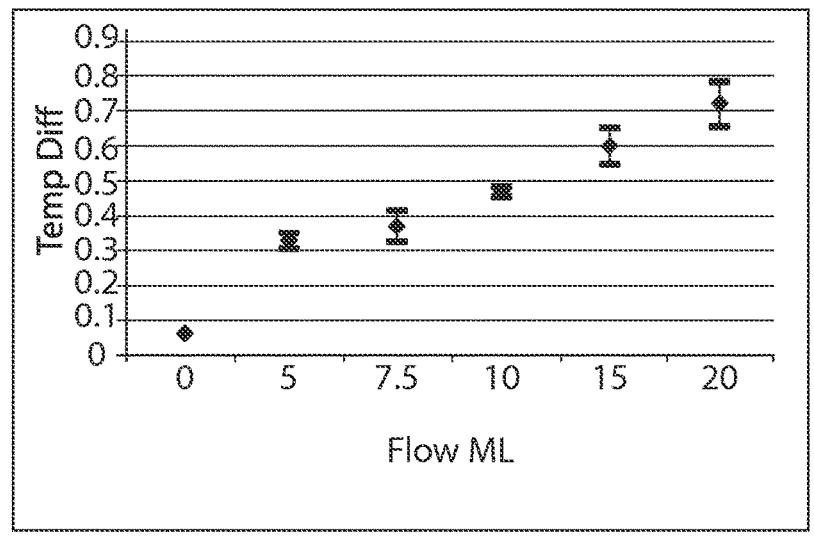
FIG. 3 is a graph showing a temperature drop vs. flow rate that is typical for the ShuntCheck thermo-dilution method.
Figure 4:
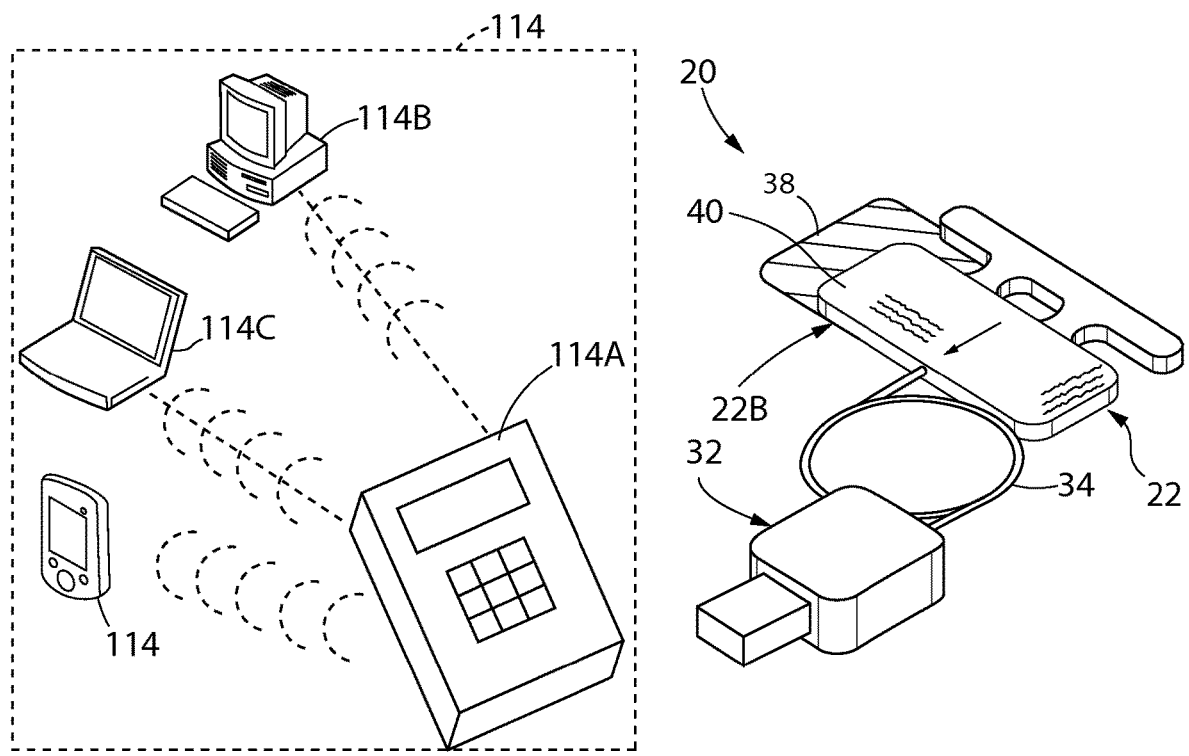
FIG. 4 is an isometric view of a first embodiment of the present invention showing the extended dynamic range (EDR) disposable thermosensor about to be coupled to a data acquisition unit for analyzing the collected temperature data and/or for relaying to a remote analyzer.

As shown most clearly in FIG. 4, the present invention 20 comprises an extended dynamic range (EDR) thermosensor 22 which is coupled to a sensor processing device 114. By way of example only, the sensor processing device 114 may comprise a data acquisition unit (DAQ) 114A that converts and conditions analog temperature sensor signals into digital format for use with, by way of example only, a workstation 114B, a laptop/tablet computer 114C, or hand-held computer device (e.g., personal digital assistant, PDA), or any known computer known in the art, etc., either wired or wirelessly, running ShuntCheck software which analyzes temperature data from the temperature sensors and provides a time-temperature graph and a flow or no-flow result. Although FIG. 4 shows the DAQ 114A relaying the data to the other computer devices, it should be understood that it within the broadest scope of the invention 20 that the DAQ may comprise the ShuntCheck software thereby collecting and analyzing the temperature sensor data itself, or the other computer devices can be coupled directly to the EDR thermosensor 22 and provide the analyzed data to the operator in that manner. Thus, it should be understood that the devices which condition and/or analyze the temperature sensor data do not form a limitation on the present invention 20. The present invention 20 may be used in conjunction with the Micro-Pumper 300, a device which generates a temporary increase in CSF flow in patent, but not in occluded, CSF shunts.

ShuntCheck was developed to help physicians differentiate patent shunts from obstructed shunts, but early ShuntCheck results indicated that patent shunts flow intermittently which meant that a no-flow ShuntCheck result did not indicate obstruction. This led to the development of the Micro-Pumper. ShuntCheck testing without Micro-Pumper 300 assesses "natural flow" through the shunt 11 while ShuntCheck testing including the Micro-Pumper 300 assesses the patency or "flow-ability" of the shunt.

Figure 5A:
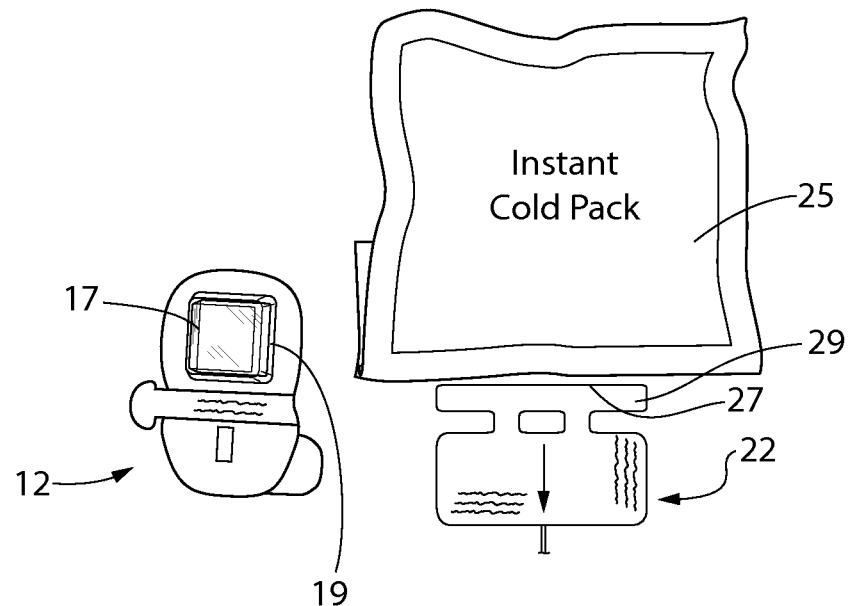
FIGS. 5A-5B compare the thermosensor of the ShuntCheck v2.2 against the EDR thermosensor of the present invention and with both thermosensors being associated with respective cold sources and with FIG. 5A showing their front sides and FIG. 5B showing their back sides.
Figure 5B:
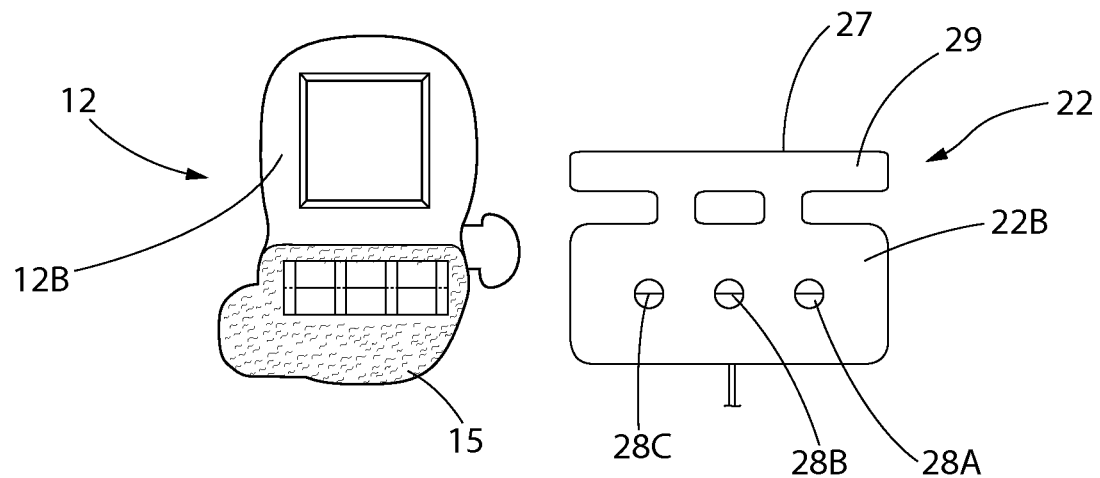

As will be described in detail later, the present invention 20 improves upon the ShuntCheck v2.2 device by providing an EDR thermosensor 22 which increases the gap between test temperature sensors (e.g., thermistors, e.g., 103JT-025 Thermistor NTC 10 kΩ manufactured by Semitec, by way of example only) and control temperature sensors (e.g., thermistors, e.g., 103JT-025 Thermistor NTC 10 kΩ manufactured by Semitec, by way of example only) of the EDR thermosensor 22 and which is also independent of the temperature source 25 (e.g., a test pack, such as a cool pack) that cools a much larger area of the skin above the CSF shunt catheter 13 and introduces a temperature pulse into the CSF. As such, the EDR thermistor 22 also increases the gap between the cold source 25 and the test/control temperature sensors 28A-28B. This distinction can be seen most clearly in FIGS. 5A-5B which shows the two thermosensors 12 and 22 side by side. In particular, in FIG. 5A, the thermosensor 12 of ShuntCheck v2.2 is shown on the left and the EDR thermosensor 22 of the present invention 20 is shown on the right. The cold source 19 used in the ShuntCheck v2.2 device is an ice cube, or an ice cube with a receptacle 17, that is positioned within a window 19 in the thermosensor 12. In contrast, in the EDR thermosensor 22, the cold source (e.g., ice pack or test pack) 25 is placed closely adjacent the EDR thermosensor 22 against the skin of the patient (not shown) when in use. FIG. 5B shows the respective back sides (12B for the ShuntCheck v2.2 and 22B for the EDR thermosensor 22 of the present invention).

Figure 6:
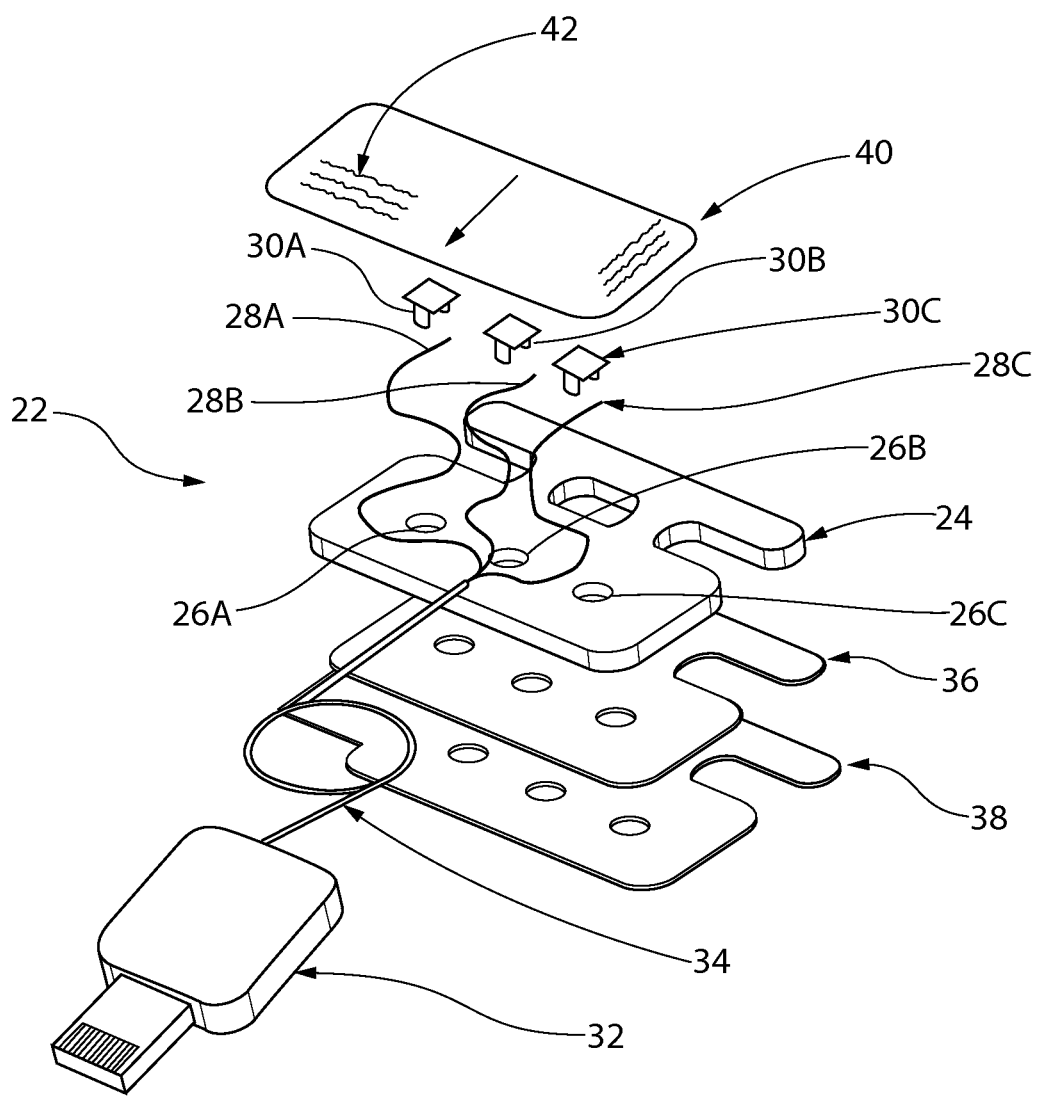
FIG. 6 is an exploded view of the EDR thermosensor of FIG. 4.
Figure 6A:
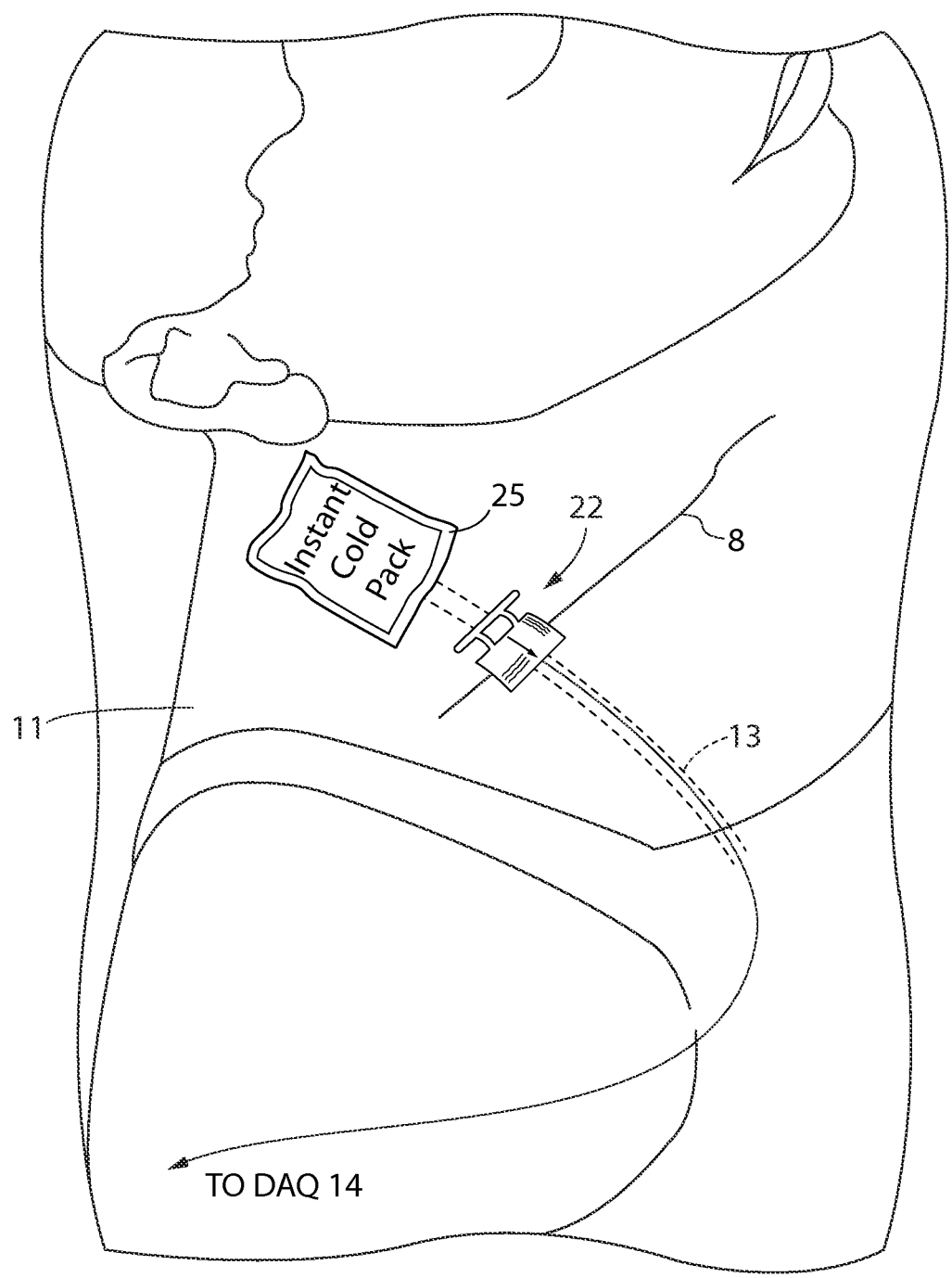
FIG. 6A shows how the EDR thermosensor is positioned on the skin of the patient over the patient's clavicle.

As shown most clearly in FIG. 6 and Table 2 below, the components of the disposable EDR thermosensor 22 are all medical grade and biocompatible. The EDR thermosensor 22 comprises a body 24 formed of, for example, an EVA (ethylene-vinyl acetate) insulated foam, having a plurality of apertures (e.g., three apertures 26A-26C) into which three respective temperature sensors 28A-28C (e.g., thermistors GE MA100BF103B or MA100BF103A or 103JT-025 Thermistor NTC 10 kΩ manufactured by Semitec, by way of example only) are positioned. In particular, the temperature sensors 28A-28C are mounted in injection-molded plastic cradles 30A-30B which are inserted into the respective apertures 26A-26C. The EVA foam insulates the temperature sensors from all temperature sources except the skin. The three temperature sensors 28A-28C, as mentioned previously, may comprise thermistors which are negative-temperature-coefficient (NTC) fast-responding (e.g., 2-second response time in still water) thermistors. The temperature sensors 28A-28C are positioned at predetermined distance PD (FIG. 8) from an upper edge 27 of the body 24; this edge is also referred to as the "ice edge" which sets the distance from a cold source 25 (e.g., ice pack, discussed below) to the temperature sensors 28A-28C. The temperature sensors 28A-28C are also positioned at fixed distances from each other. Each temperature sensor 28A-28C is electrically coupled to a connector 32 (e.g., Inteprod connector box RJ45 connector) via a wire harness or cable 34. By way of example only, where thermistors are used, two wires from each thermistor may be soldered to a single flexible cable (e.g., 22.3 cm in length) comprising six internal wires; these wires may be soldered to the connector 32 (e.g., RJ45 (Ethernet-type) connector) that is compatible with a jack mounted on or within the DAQ 114A. The back side 22B of the EDR thermosensor 22 comprises an adhesive layer 36 (e.g., I-832 adhesive item #MED 5634) which is covered by release liner 38. A label 40 with indicia 42 thereon (e.g., instructions on how to properly align the EDR thermosensor 22 when securing it to the skin of the patient) is secured to the front side 22A of the body 24. The EDR thermosensor 22 is applied to the patient's skin by first removing the release liner 38 and then adhering the thermosensor 22 directly to the skin 11, for example, over the clavicle 8 of the patient as shown in FIG. 6A.

TABLE 2

Performance Characteristics of the Thermosensor Array Patch

| Thermosensor element | Manufacturer: model | Performance Characteristic | Contacts Patient? |
|---|---|---|---|
| EVA Foam with adhesive film and paper backing | Avery Dennison MED 5634 | Forms the body of the patch Adheres patch to skin Protects adhesive | Yes |
| Thermistors | GE: MA100BF103B or GE: MA100BF103A | Collects temperature data with a response time of 2 seconds | Yes |
| Cable | GE: MA100BF103B or GE: MA100BF103A | | No |
| Connector | Inteprod connector box RJ45 connector | | No |
| Thermistor cradles | Rynel Lexan HP2 | Holds thermistors in foam | Yes |
| Label | Avery | Identifies Orientation of Thermosensor to Shunt | No |

Figure 7:
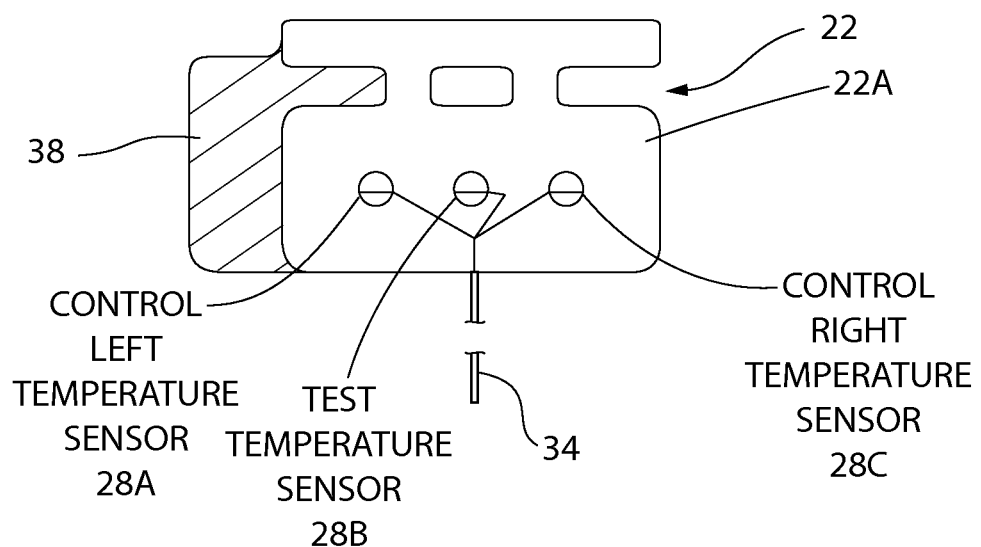
FIG. 7 is top view of the EDR thermosensor 22 with the label removed.
Figure 8:
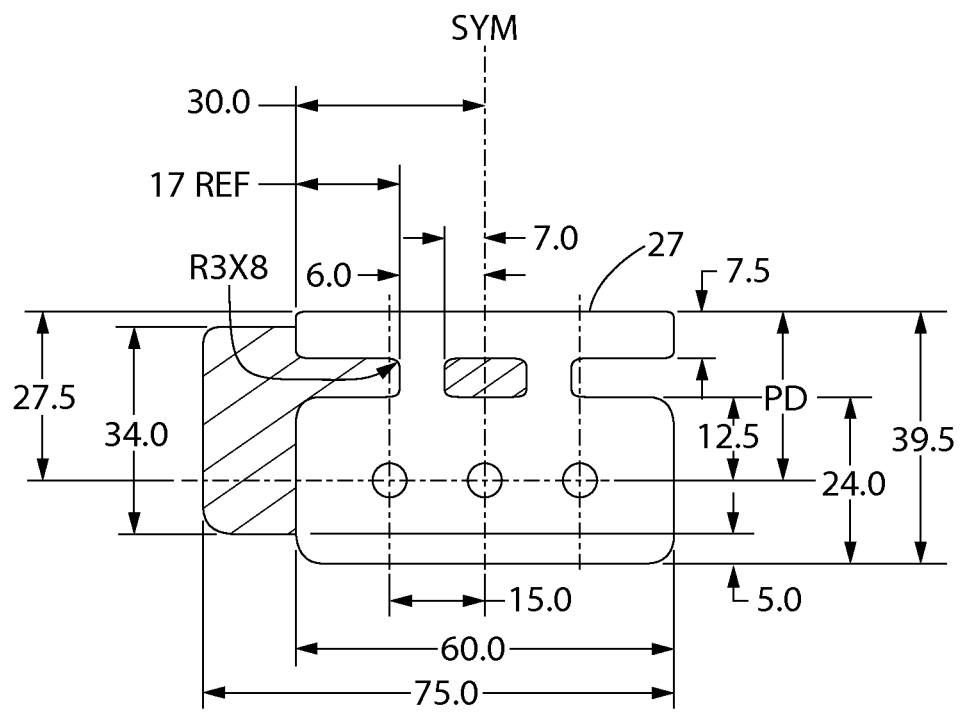
FIG. 8 depicts exemplary dimensions of the EDR thermosensor of the present invention.

FIG. 7 is top view of the EDR thermosensor 22 with the label 40 removed showing the relative positions of the two control temperature sensors 28A and 28C and the test temperature sensor 28B. FIG. 8 depicts exemplary dimensions of the EDR thermosensor 22.

The cold pack 25 (e.g., 3"×3") provides a significantly larger cold temperature source than the ice cube 17, or ice cube in receptacle used in ShuntCheck v2.2. A T-shaped member 29 (see FIGS. 5A-5B) having upper edge 27 at the top of the EDR thermosensor 22 guides the operator to place the cooling source 25 at uniform and equal distance from the test temperature sensor 26B and the control temperature sensors 28A/28C. The preferred separation distance (SD) is 16mm <SD ≤36mm. See FIG. 8. If the separation distance is less than 16mm, this results in too much ambient skin cooling that reaches the sensors 28A-28C, thereby creating test "noise". If, on the other hand, the separation distance SD is greater than 36mm, this lengthens the test time and reduces the test signal, since the chilled CSF rewarms as it moves down the shunt 13. A specific distance in the range of 24 to 28mm combined with ice-on time of 60 seconds strikes an optimal balance in cold-to-sensor distance and thermal input. The control thermistors 28A/28B are 15mm (center-to-center) from the test thermistor 28B, reducing impact of minor misalignment on test results.

The preferred embodiment of the cold source 25 is an instant cold pack, specifically 4"×6" over-the-counter instant ice pack used according to label (thereby eliminating the need for ice stored in a freezer). As shown in FIG. 5A, the ice pack 25 is placed along the top edge 27 of the thermosensor 22, at a separation distance SD of 28 mm from the temperature sensors 28A-28C. The combination of the larger ice "footprint" and the greater ice-to-temperature sensor distance allows EDR thermosensor 22 to detect a wider range of shunt flows.

Figure 5C:
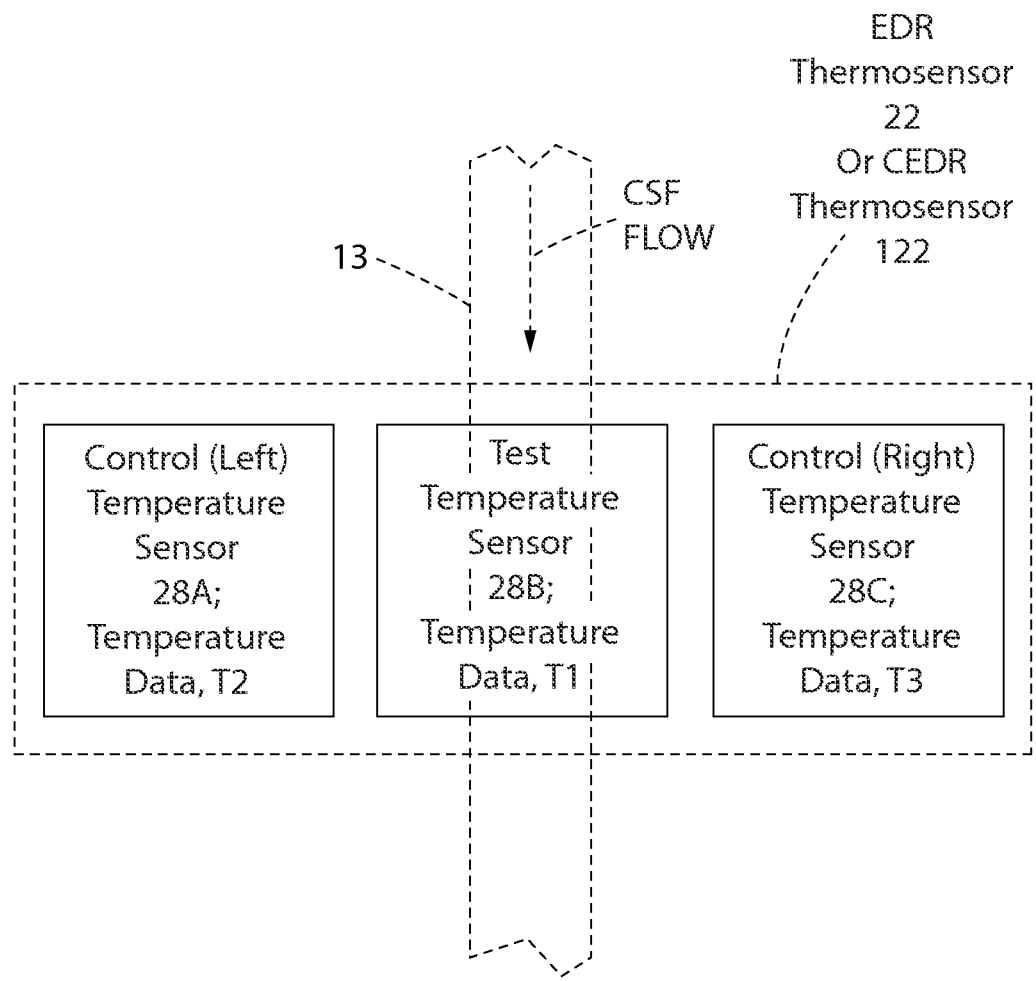
FIG. 5C is a functional diagram showing the relationship of the temperature sensor data designators with regard to the temperature sensors used in the disposable pad.

In general, the temperature sensor data from the plurality of sensors 28A-28C is analyzed by the sensor processing device 114 to yield a differential temperature signal, (also referred to as "resultant temperature signal") based on:

$$T1-(T2+T3)/2$$

where T1 represents temperature sensor data from the test sensor aligned over the shunt 13, namely, sensor 28B, while T2 and T3 represent the temperature sensor data from the control sensors 28A and 28C, respectively, located on opposite sides of the shunt 13. Thus, the average of the control sensor data is subtracted from the test temperature sensor data, in accordance with U.S. Patent Publication No. 2011/0054382. FIG. 5C provides a functional diagram that associates the plurality of temperature sensors with the differential temperature signal.

Figure 16A:
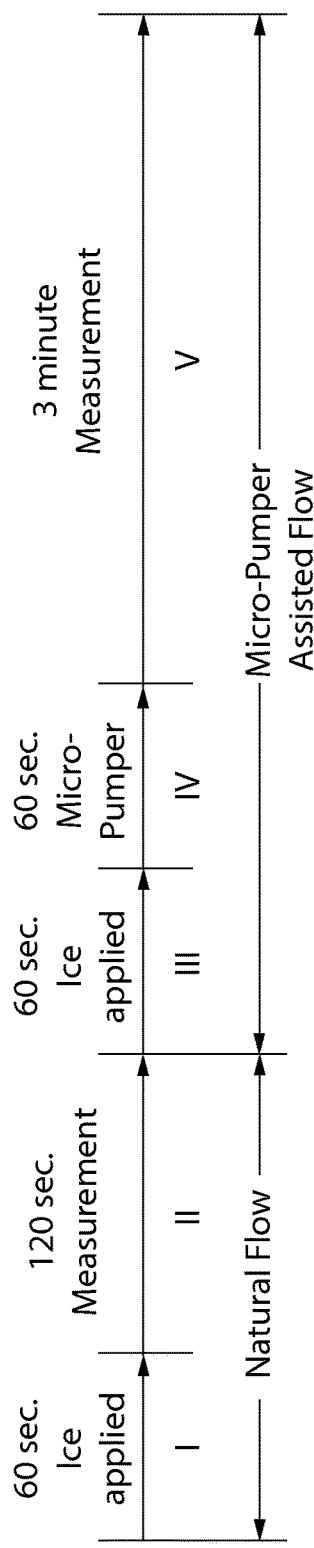
FIG. 16A is a timing diagram for a natural flow and Micro-Pumper flow test procedure.
Figure 16B:
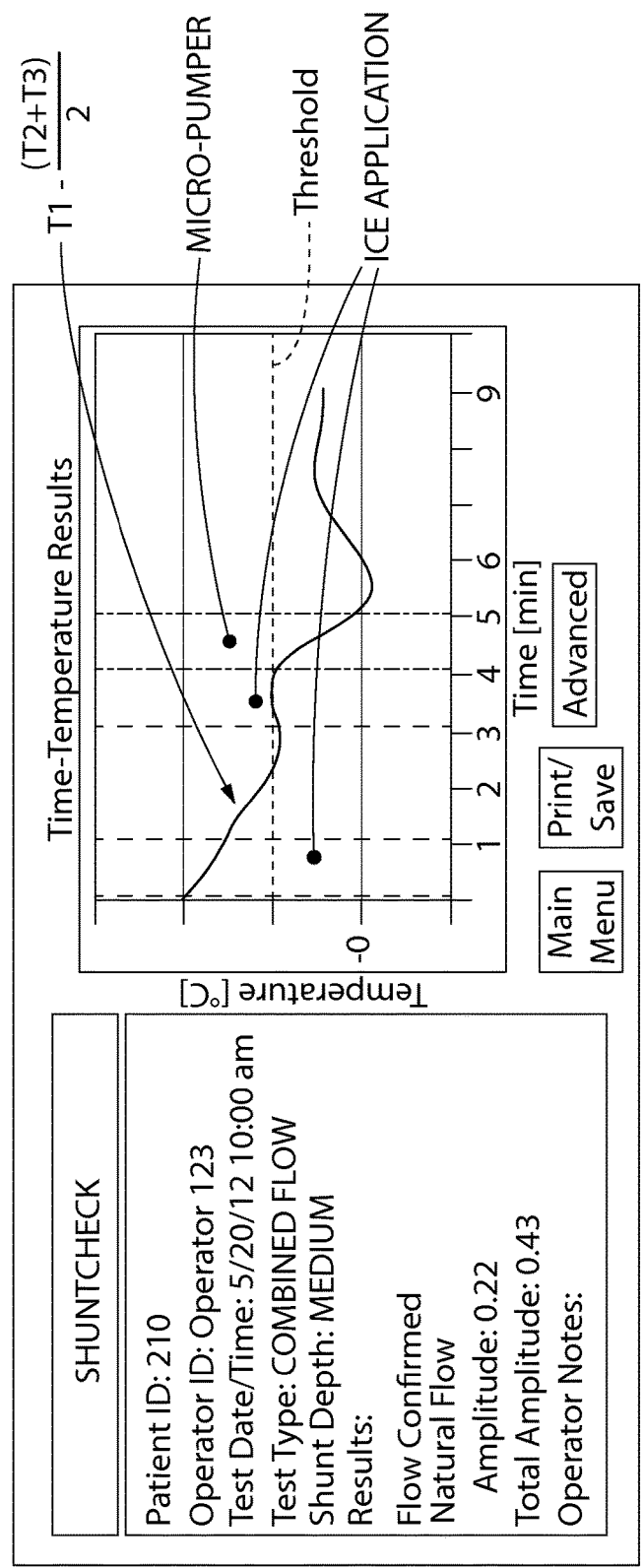
FIG. 16B is an exemplary display screen depicting patient information using the ShuntCheck device which includes the CEDR thermosensor.

The ShuntCheck software in the analyzer 114 uses this data to compare it to a threshold to determine if CSF flow is present or not. A CSF flow rate can then also be automatically determined from monitoring the CSF flow over time. The threshold is determined by the geometry of the EDR thermosensor 22 and the temperature source 25. In particular, how far the temperature sensors 28A-28C are displaced from the temperature source 25, how far the temperature sensors 28A-28C are spread apart, and the "power" and geometry of the temperature source 25. FIG. 16B, by way of example only, shows the curve T1–(T2+T3)/2 having a "flow confirmed" threshold of –02° C.

Furthermore, it is desirable to determine an approximation of the steady state of the differential temperature signal. The approximation for this steady state can be represented as the lowest point in the curve T1–(T2+T3)/2. The steady state occurs when the cooling source 25, and CSF flow rate are constant and continuous. For a certain geometry (e.g., depth, passageway size) and certain flow rate, a continuous cooling source 25 generates a particular distribution of temperatures. The lowest point on the graph (e.g., see FIG. 16B) can be treated as an approximation of this steady state. The difference T1–(T2+T3)/2 eliminates, to a certain extent, temperatures caused by other sources of heating/cooling (e.g., bio heat) and other than shunt heat conductors (e.g., arteries). This "lowest point," referred to as $T_{sensor}$ is given by:

$$T_{Sensor} = T_{CSF} + (2\pi RQL_{shunt})/\rho cF$$

where $T_{CSF}$ $$T_{CSF} = \Delta T e^{\left(-\frac{L_{ice}}{F^2 kc}\right)} + T_{cold}$$

Where $T_{CSF}$=CSF temperature;
ΔT=Temperature difference between normal body temperature and cold tissue cooled by the ice cube (assumed to be 15° C.);
$T_{cold}$=cold tissue temperature;
R=shunt radius;
Q=rate of heat exchange;
$L_{ice}$=length of the ice cube;
$L_{shunt}$=distance between ice cube and the sensor;
ρ=specific density of CSF;
c=specific heat of CSF;
k=specific conductivity of CSF; and
F=CSF flow rate.

This ShuntCheck algorithm or formula can be used to assess monotonic range for the thermosensor 22, as well as the influence of the distance ($L_{shunt}$) between the ice pack 25 and the temperatures sensors 28A-28C and the ice pack 25 length on the temperature drop. Although skin temperatures will be much higher than those predicted by the formula, and depend on skin thickness and bio-heat level, the maximum of the temperature curve will hold its position.

Figure 9:
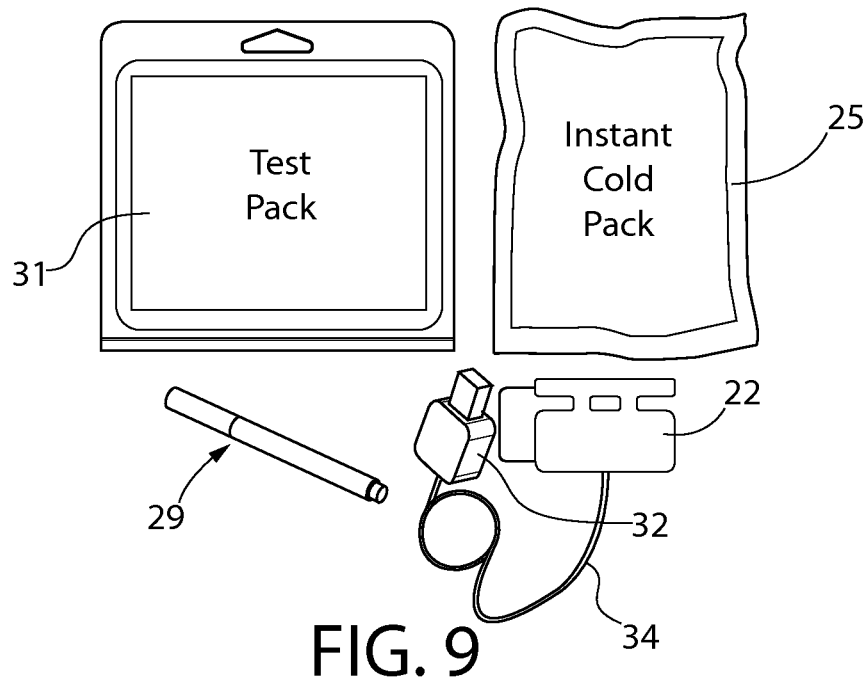
FIG. 9 depicts an exemplary kit for the EDR thermosensor.

The EDR thermosensor 22, the instant ice pack 25 and a single use, commercially available skin marker pen 29 are packaged in a plastic clamshell 31 to form a kit (see FIG. 9). This ensures that all single use items used in a test procedure are combined in a convenient single pack.

Bench testing demonstrates that the EDR thermosensor 22 plus the instant cold pack 25 cooling method can detect the robust, temporary shunt flow generated by using the Micro-Pumper 300, as shown in Table 3, can detect lower levels of shunt flow than could be detected by the v2.2 thermosensor, as shown in Table 4 and is less sensitive to minor misalignment errors as shown in Table 5.

TABLE 3

ShuntCheck III Results for Typical Flow Conditions

| Flow Before MP (ml/hr) | Flow During MP (ml/hr) | Flow After MP (ml/hr) | Results | % Flow Not Confirmed | % Flow Confirmed |
|---|---|---|---|---|---|
| 0 | 0 | 0 | Flow Not Confirmed | 100% | — |
| 0 | 15 | 0 | Flow Confirmed) | — | 100% |
| 0 | 50 | 0 | Flow Confirmed | — | 100% |
| 0 | 100 | 0 | Flow Confirmed | — | 100% |
| 10 | 15 | 10 | Flow Confirmed | — | 100% |
| 10 | 50 | 10 | Flow Confirmed | — | 100% |
| 10 | 100 | 10 | Flow Confirmed | — | 100% |
| 10 | 200 | 10 | Flow Confirmed | — | 100% |

TABLE 4

Bench Test Results for ShuntCheck III vs v2.2 at a Range of Flow Rates

| | Actual Flow [ml/hour] | | | | | | |
|---|---|---|---|---|---|---|---|
| | 0 | 3.5 | 4.25 | 5 | 7.5 | 10 | 20 |
| ShuntCheck III % Flow Confirmed On Thermal Bench | 0 | 0 | 30 | 100 | 100 | 100 | 100 |
| ShuntCheck v2.2% Flow Confirmed on Thermal Bench | 0 | N/A | N/A | 0 | 70 | 90 | 100 |
| ShuntCheck v2.2% Flow Confirmed from previous 510(k) testing on Porcine model | 0 | N/A | N/A | 0 | 70 | 90 | 100 |

TABLE 5

Comparison Test Results for ShuntCheck III and ShuntCheck v2.2 at with Placement Misalignments

| | Positional Misalignment | 2 mm | 4 mm | 6 mm |
|---|---|---|---|---|
| EDR Thermosensor 22 | Number "Flow Confirmed" | 5 | 10 | 9 |
| | Number of "Flow Not Confirmed" | 0 | 0 | 1 |
| | % Flow Confirmed | 100 | 100 | 90 |
| ShuntCheck v2.2 Thermosensor | Number "Flow Confirmed" | 5 | 0 | 0 |
| | Number of "Flow Not Confirmed" | 0 | 5 | 5 |
| | % Flow Confirmed | 100 | 0 | 0 |

Therefore, the EDR Thermosensor 22 plus the larger cooling source 25 (e.g., the instant cold pack) when used in conjunction with the DAQ 114A: (1) permit the detection of the robust, temporary CSF flow generated by the Micro-Pumper 300; (2) permit the detection of the lower level of CSF flow common in pediatric patients; and (3) are less sensitive to minor misalignment errors.

To address test variability caused by differing catheter depth, two easy-to-use methods have been developed for assessing shunt depth and a method for adjusting the Shunt-Check result to compensate for differing depths.

Catheter depth at the clavicle (e.g., the preferred site of the ShuntCheck thermal reading; see FIG. 6A) can be measured by pinching the patient's at the clavicle, measuring the thickness with a caliper and dividing the measurement by 2. Preliminary assessments have determined that the skin thickness at the clavicle is approximately 5 mm but wherein that value can be adjusted as more test data is obtained.

An alternative method is for the test operator to classify patients into groups based upon palpation of the shunt at the clavicle. Patients whose catheter creates a visible ridge on the clavicle can be classified as thin skin or shallow shunt depth. Patients whose catheter is not visible but is easily palpated would be classified as medium skin thickness or shunt depth. Patients whose catheter can be palpated but with difficulty are classified as thick or deep. Patients whose catheter cannot be palpated are classified as very thick very deep. For thin skin (wherein preliminary data suggests is about ½ average thickness), the temperature drop is adjusted down 50% (e.g., a reading of 0.8° C. would be adjusted to 0.4° C.). For thick skin (which wherein preliminary data suggests is about 2 times average thickness), the temperature drop is adjusted upward by 100% (e.g., a 0.2° C. reading is adjusted to 0.4° C.).

The ShuntCheck result, which is a temperature change measurement, can be adjusted by the equation:

$$\text{Temperature Drop adjusted} = \text{Temperature Drop} \times \text{Actual Skin Thickness} / \text{Average Skin Thickness}.$$

During the ShuntCheck process, the computation of the adjusted temperature drop is accomplished as follows: The test operator takes the caliper or palpation reading before ice pack placement and inputs the data into the sensor processing device 14 which comprises the ShuntCheck software. The ShuntCheck software containing the algorithms or formulae discussed above, adjusts the temperature data and either reports only the adjusted result or the actual and adjusted result. Thus, it should be understood that the embodiment 20 of the present invention is also an apparatus/method for measuring changes in skin temperature above a subcutaneous CSF shunt.

Figure 10:
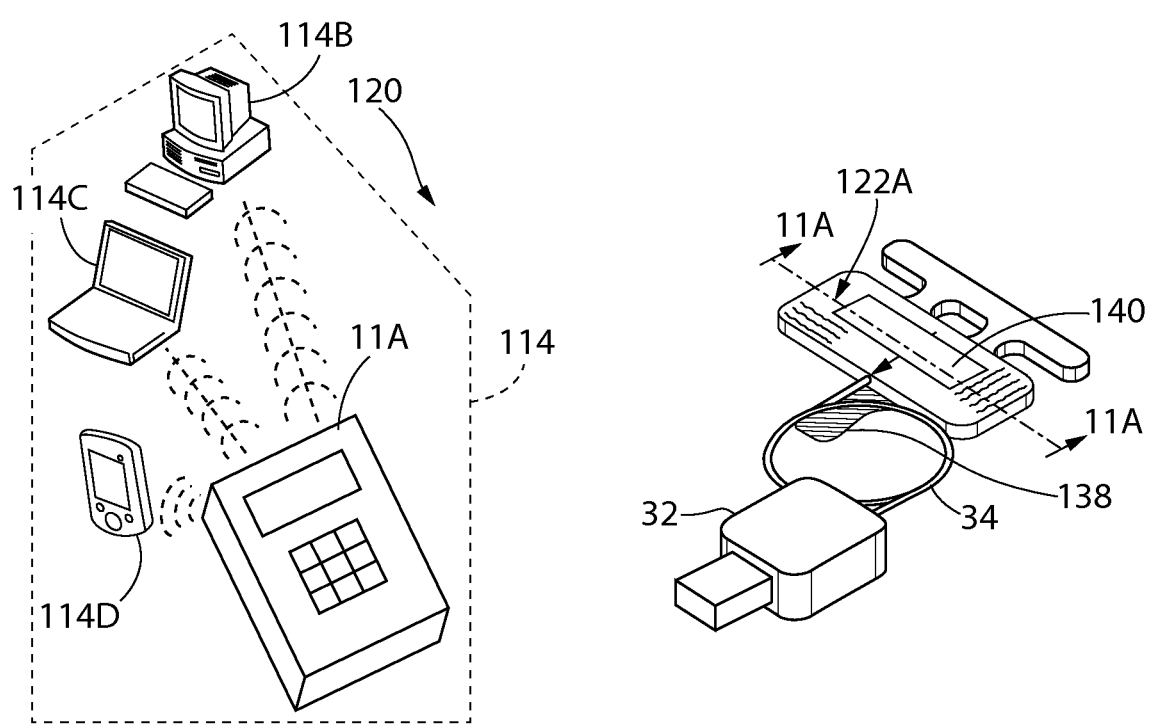
FIG. 10 is an isometric view of a second, more preferred, embodiment of the present invention showing the conformable extended dynamic range (CEDR) disposable thermosensor about to be coupled to a data acquisition unit for analyzing the collected temperature data and/or for relaying to a remote analyzer.

A second more preferred embodiment 120 of the present invention is shown in FIG. 10. In this embodiment the EDR thermosensor 22 has been replaced with a conformable EDR thermosensor 122, hereinafter referred to as the "CEDR thermosensor 122." As with the EDR thermosensor 22, the CEDR thermosensor 122 is disposable. Similarly, the CEDR thermosensor uses a plurality of temperature sensors (e.g., thermistors GE MA100BF103B or MA100BF103A or 103JT-025 Thermistor NTC 10 kΩ manufactured by Semitec, by way of example only) which are also referenced as 28A-28C. The CEDR thermosensor 122 couples to the data acquisition unit 114 that analyzes the collected temperature data and/or relays such data to a remote analyzer (not shown). As with the first embodiment 20, the second embodiment 120 is coupled to the sensor processing device 114 which operates in the same manner and is therefore not discussed further. The present invention 120, as with the first embodiment 20, may be used in conjunction with the Micro-Pumper.

Figure 15:
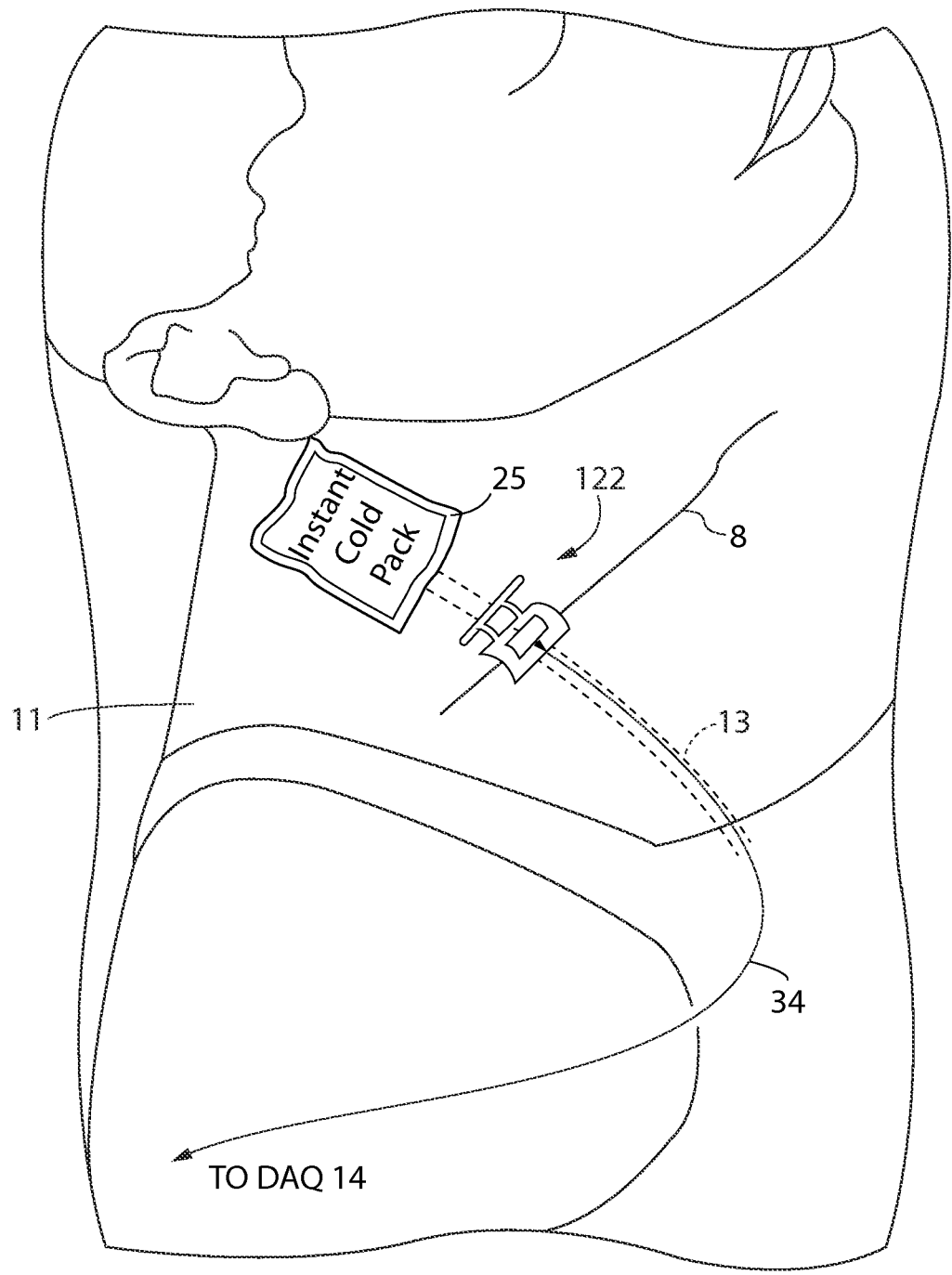
FIG. 15 shows how the CEDR thermosensor is positioned on the skin of the patient while properly conforming to the patient's clavicle.

It is desirable to releasably secure the thermosensor over the patient's clavicle 8 because the shunt catheter 11 is easy to locate via palpation and few major blood vessels which can interfere with the ShuntCheck thermal signal cross the clavicle. However, because the clavicle 8 comprises a curved surface, it does pose a mechanical challenge for temperature sensor signals, namely, if the thermosensor does not wrap around and adhere tightly to the clavicle, the sensor pad lifts up away from the skin, thereby most likely generating faulty thermal readings. To that end, Applicant has designed the CEDR thermosensor 122 which comprises a flexible design (as discussed below), especially for adhesive placement on the patient where the shunt 11 crosses the clavicle 8 (see FIG. 15). Furthermore, the CEDR thermosensor 122 also minimizes the conduction of heat or cold to the temperature sensors that can be introduced from the flex circuit leads which could introduce error into the temperature sensor readings.

Figure 11:
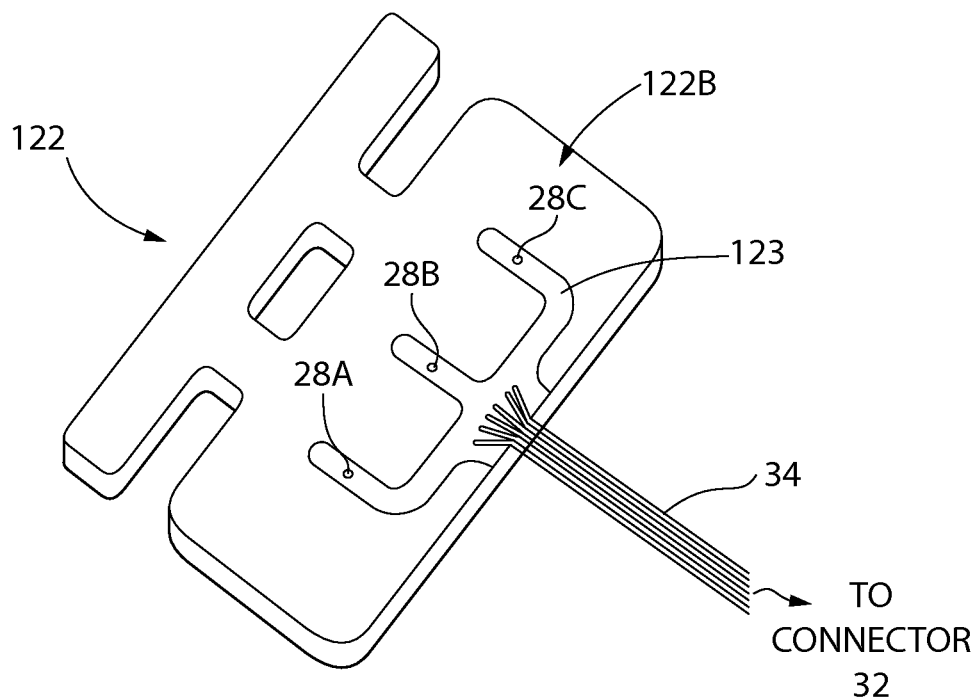
FIG. 11 is a plan view of the CEDR disposable thermosensor depicting the flex circuit that is applied directly against the skin of the patient, with the corresponding cable shown partially.
Figure 13A:
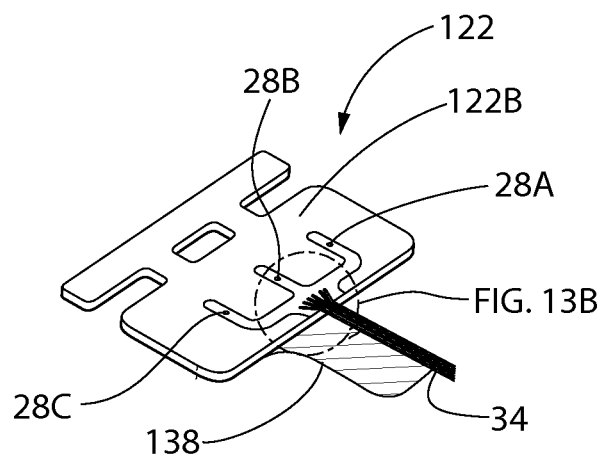
FIG. 13A is a plan view of the CEDR disposable thermosensor showing the cable coupled to the flex circuit.
Figure 13B:
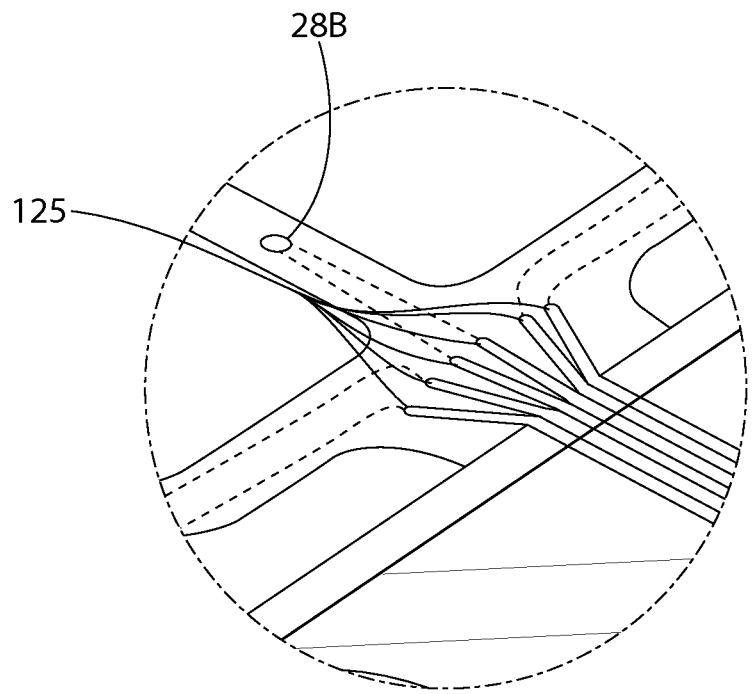
FIG. 13B is an enlargement of a portion of the flex circuit of FIG. 13A showing the cable connection to the flex circuit.

In particular, as shown most clearly in FIG. 11, the CEDR thermosensor 122 has a side 122B that is adapted to be adhesively-coupled to the patient's skin 11, especially over the clavicle 8. Side 122B comprises an "E-shaped" flex circuit 123 upon which the temperature sensors 28A-28C are mounted. The E-shaped flex circuit 123 in turn is mounted on the body of the CEDR thermosensor 122, e.g., a foam pad. The E-shaped flex circuit 123 minimizes the bulk of the circuit leads near the temperature sensors 28A-28C (see FIGS. 13A-13B), thereby reducing thermal conductivity and therefore thermal crosstalk between the temperature sensors 28A-28C which yields higher quality temperature signals. It also enhances the conformability of the flex circuit 123 and therefore the conformability of the overall thermosensor 122 since the flex material (e.g., polyimide) is malleable; thus, the flex material is stiff and cannot be stretched but it can be bent or curved in multiple directions. As a result, not only the segments or prongs of the E-shaped flex circuit 123 can be bent but the long side that connects all of them can also be bent or curved. The E-shaped legs or traces is key to conformability by allowing simultaneous bending in two directions, along and around the clavicle 8.

Figure 11A:
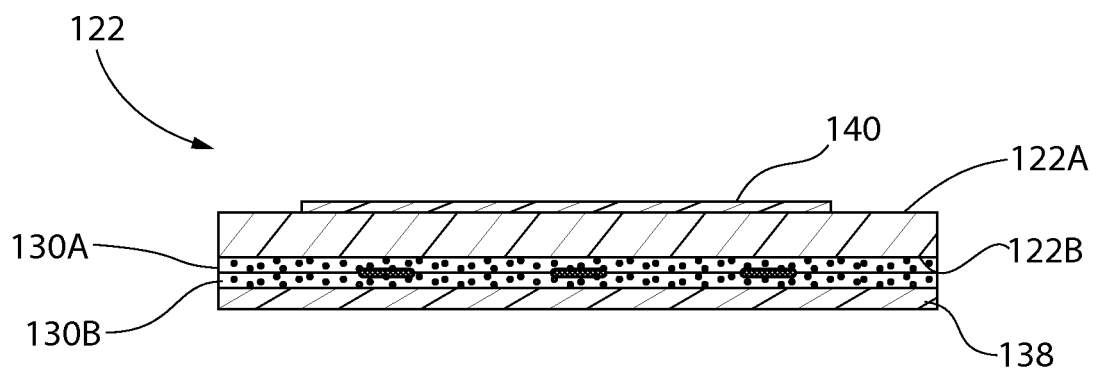
FIG. 11A is an enlarged cross-sectional view of the CEDR thermosensor taken along line 11A-11A of FIG. 10.

The flex circuit 123 and the temperature sensors 28A-28C mounted on the circuit 123 are flat and therefore create no upward pressure on the pad when placed on the skin 11 since there are no protrusions. The lack of protrusions also allows the entire surface 122B with adhesive layers 130A/130B (see FIG. 11A) to be in contact with the skin 11 providing more surface area with adhesive. This also eliminates the leverage that the non-adhesive areas around the protrusion had—which made it peel off more easily from the skin since in effect it had already begun to peel. Thus, the omission in the CEDR thermosensor 122 of the cradles 30A-30C of the EDR thermosensor 22 that hold the temperature sensors 28A-28C enhances conformability and skin adhesion.

Figure 12:
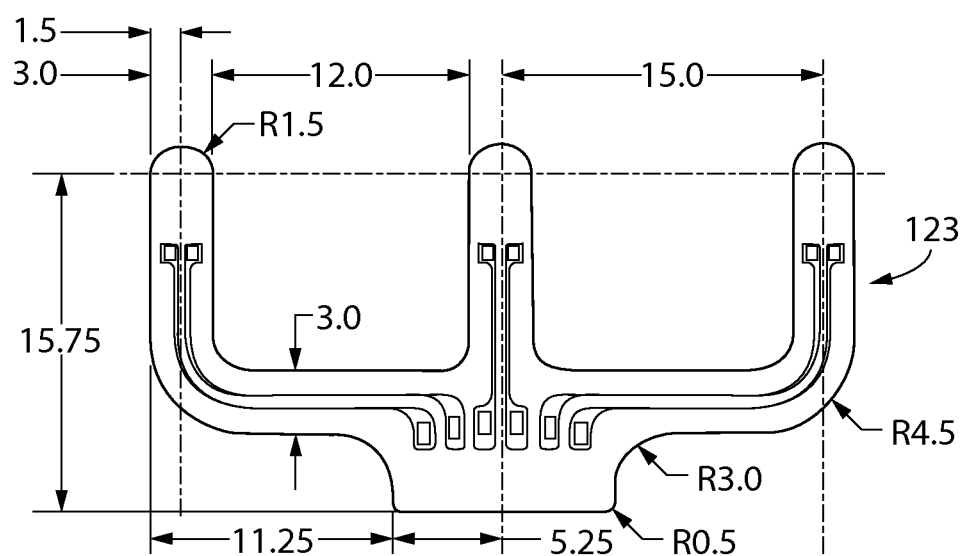
FIG. 12 depicts exemplary dimensions of the CEDR thermosensor of the present invention.

FIG. 12 provides dimensions of the CEDR thermosensor 122 by way of example only. The polyimide material of the flex circuit legs 122 are only 3 mm wide. This constructions is also an improvement over the EDR thermosensor 22 by reducing thermal conductivity between the temperature sensors 28A-28C since polyimide is more conductive than the foam pad and improves the CEDR thermosensor 122 conformability.

The flex circuit 123 leads are approximately 4 mil wide traces of copper (see FIG. 12), which are thinner than the more typical 10 mil traces. This further reduces thermal conductivity to more slowly transfer temperature from other non-desirable points (e.g., along the traces), which otherwise result in averaging and inaccuracy for the temperature measurement at the precise point desired and further improves conformability; see data in Table 6 below.

To secure the flex circuit 123 to the insulating foam pad of the thermosensor side 122B, a first adhesive layer 130A is applied on side 122B and the flex circuit 123 is applied thereon.

The flex circuit 123 is then covered with a second adhesive layer 130B which holds the thermosensor 122 on the patient's skin 11. This second adhesive layer maximizes skin adhesion and reduces the risk of poor sensor-to-skin contact. This second adhesive layer keeps the individual temperature sensors 28A-28C secured to the pad 122 and the temperature sensors secured to the skin 11 because there is an adhesive layer on both sides of the temperature sensors 28A-28C and the flex circuit 123, resulting in lower noise since temperature sensors (e.g., thermistors) move with and do not lift off the skin; see data in Table 7 below.

Both layers of adhesive 130A/130B are adhesive only. This compares to many adhesive applications where the adhesive comes mounted on a carrier material. Using a carrier-free adhesive enhances conformability A sensor label 140 (FIG. 10) comprises a thin, flexible lower modulus (i.e., less stiff) material (low-density polyethylene (LDPE) vs typical polyester) allowing it to strain (stretch) easier in tension in multiple directions, enhancing conformability.

In a preferred embodiment of the CEDR thermosensor 122, the sensor label 140 is omitted and product information is printing directly on the top surface 122A of the foam pad 122, further enhancing conformability.

The flex circuit 123 is fixedly secured 125 (e.g., soldered; see FIG. 13B) to the sensor cable at the distal end of the thermosensor pad 122 and the solder joint is sandwiched between the two layers of adhesive. This strengthens the cable 34-to-pad 122 connection which allows a lift tab 127 (FIGS. 10 and 13A) on the adhesive release paper to be located at the bottom of the thermosensor pad 122. The user can grip the sensor cable 34 while peeling up the liner paper 138. This makes that operation easier to complete and reduces the risk of the liner paper 127 tearing. The large inside radii (8 mm) of the liner where it meets pad also reduces susceptibility for tearing. It also allows the user to remove the sensor pad from the patient's skin by pulling up on the sensor cable.

The flex circuit 123 design allows the use of a non-custom flat cable and an RJ-45 connector, also reducing cost of goods. Alternatively, a telephone-style jack can also be used for the connector.

The components (see Table 6 below) of the disposable CEDR thermosensor 122 are all medical grade and biocompatible. As discussed above, the CEDR thermosensor 122 comprises layering a number of adhesive and insulating materials formed to specific dimensions and shape. The configuration of the CEDR thermosensor 122 array patch is shown in FIG. 12. The body of the thermosensor 122 comprises an EVA insulated foam. The plurality of temperature sensors comprises three thermistors that are surface mount devices and are soldered 125 to the flexible printed circuit 123 which is adhered to the EVA foam. As with the EDR thermosensor 22, the EVA foam in the CEDR thermosensor 122 insulates the thermistors from all temperature sources except the skin. The three thermistors are NTC fast-responding (2.2 second response time in air) obtained from a commercial supplier (Semitec), and are arranged at precise distances from the upper edge of the EVA foam (the ice edge which sets the distance from the ice pack and the thermistors) and from each other. The flexible printed circuit traces are soldered to a cable 34 (e.g., a single flat ribbon flexible cable (e.g., 60 cm in length) comprising six conductors) These conductors are attached to an RJ45 (Ethernet-type) connector 32 that is compatible with a jack mounted on the DAQ 114A. A label 140 indicating the correct placement and orientation of the CEDR thermosensor 122 array patch is adhered to the uppermost surface. A medical grade adhesive with a disposable protective paper layer on one side is placed over the flexible circuit board 123. The CEDR thermosensor 122 array patch is applied by first removing this paper layer and then adhering the patch directly to the skin 11.

TABLE 6

Performance Characteristics of the CEDR Thermosensor Array Patch

| Thermosensor element | Manufacturer: model | Performance Characteristic | Contacts Patient? |
|---|---|---|---|
| EVA Foam with adhesive film | Avery Dennison MED 5634 | Forms the body of the patch | No |
| Thermistors | Semitec: 103KT1005T-1P | Collects temperature data with a response time of 2 seconds | No |
| Cable | 3M: 3756 series, Round Conductor Flat Cable, 30 AWG, TPE | TPE material provides better soldering ability because it has higher melting temp. | No |
| Connector | RJ45 connector | Using 28 gauge connector with 30 ga flat cable allows it to be assembled because of flash between conductors after separation allowing reduced cost | No |
| Adhesive Layer | 3M product #1524 | Attaches to patient | Yes |
| Label | Avery | Identifies Orientation of Thermosensor to Shunt | No |

Figure 14:
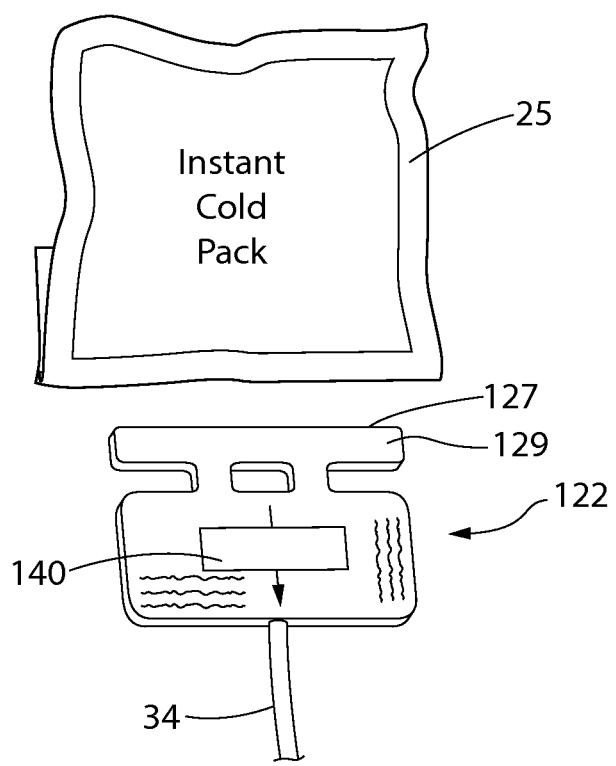
FIG. 14 shows a cold source applied in close proximity to the CEDR thermosensor of the present invention using the upper "ice edge" of the thermosensor to properly place the cold source.

As with the EDR thermosensor 22, the preferred embodiment of the cold source 25 for use with the second embodiment 120 is also an instant cold pack for introducing a temperature pulse into the CSF, discussed previously. As shown most clearly in FIG. 14, a T-shaped member 129 having an upper edge 127 at the top of the CEDR thermosensor 122 guides the operator to place the cooling source 25 at uniform and equal distance from the test sensor 28B and the control temperature sensors 28A/28C. The separation distance SD discussed previously with the EDR thermosensor 22 applies to the CEDR thermosensor 122 and, as such, is not repeated here. Similarly, the CEDR thermosensor 122 forms a portion of another ShuntCheck Test Pack, similar to the kit discussed previously with regard to FIG. 9. As such, the kit including the CEDR thermosensor 122 also includes a marker for placing a skin marker "upstream" of the CSF flow from the CEDR thermosensor 122, to cool the CSF in the shunt 13. Thus, the temperature sensors 28A-28C placed over the shunt 13 detect the change in temperature as cooled fluid flows beneath them. The presence of flowing fluid is interpreted as a decrease in temperature detected by the temperature sensors, while no change in temperature indicates the absence of flow. In addition, the ShuntCheck algorithm or formula discussed previously with respect to the first embodiment 20, applies to the second embodiment 122 and is therefore also not repeated here.

Data in Table 7 below shows 22% lower (better) Short Term Noise (STN) for the CEDR thermosensor 122 vs the EDR thermosensor 22. ShuntCheck tests on unshunted skin without ice were run and the noise value calculated by the ShuntCheck software was compared for each thermistor. The noise algorithm accumulates the deviations from the average over a fixed period (10 s).

TABLE 7

Short term noise data

| run order | Thermosensor | t1 (Sensor 28B) | t2 (sensor 28A) | t3 (sensor 28C) | |
|---|---|---|---|---|---|
| 1 | EDR 22 | 0.43 | 0.41 | 0.67 | |
| 2 | EDR 22 | 0.44 | 0.44 | 0.53 | |
| 3 | EDR 22 | 0.46 | 0.46 | 0.72 | |
| 1 | CEDR 122 | 0.47 | 0.39 | 0.39 | |
| 2 | CEDR 122 | 0.4 | 0.37 | 0.35 | |
| 3 | CEDR 122 | 0.47 | 0.36 | 0.35 | |
| | avg-EDR | 0.44 | 0.44 | 0.64 | .51 |
| | avg-CEDR | 0.45 | 0.37 | 0.36 | .39 |
| | T-test | 0.9035 | 0.0286 | 0.0340 | |
| | Effect (delta) | 0.00 | 0.06 | 0.28 | .11 |
| | 3 run avg of t1, t2, t3 EDR | | | 0.51 | |
| | 3 run avg of t1, t2, t3 CEDR | | | 0.39 | |
| | Delta | | | 0.11 | |
| | CEDR short term noise improvement over EDR | | | 22% | |

The data in Table 8 below shows that 4 mil wide traces yield an average improvement in ShuntCheck signal Amplitude of about 10% over 10 mil wide traces. ShuntCheck tests were run using a heated bench test fixture that simulates a flowing implanted shunt at skin temperature with a syringe pump attached to control the flow rate.

It should also be understood that the preferred embodiment 120 also forms an apparatus/method for measuring changes in skin temperature above a subcutaneous CSF shunt as discussed previously with regard to the embodiment 20.

TABLE 8

| Trace Width | Signal Amplitude @ 10 ml/hr |
|---|---|
| 4 | 0.65 |
| 4 | 0.64 |
| 4 | 0.65 |
| 4 | 0.67 |
| 4 | 0.52 |
| 4 | 0.66 |
| 4 | 0.64 |
| 4 | 0.66 |

TABLE 8-continued

| Trace Width | Signal Amplitude @ 10 ml/hr |
| --- | --- |
| avg | 0.64 |
| sd | 0.05 |
| 10 | 0.63 |
| 10 | 0.64 |
| 10 | 0.6 |
| 10 | 0.54 |
| 10 | 0.49 |
| 10 | 0.56 |
| 10 | 0.63 |
| 10 | 0.57 |
| avg | 0.58 |
| sd | 0.05 |
| ttest | 0.05 |
| effect | 0.05 |
| 4 vs 10 mil avg improvement | 0.05 |
| avg 10 mil | 0.58 |
| % Improvement of 4 mil over 10 mil | 9% |

Error Check for Quantifying Signal Noise Based on Poor Sensor-to-Skin Contact

The present invention 20/120 also comprises an error check for quantifying signal noise based on poor sensor-to-skin contact and to alert the user in both a pre-test setting and a post-test setting. Thus, both inventions 20/120 also form an apparatus/method for quantifying temperature sensor signal noise generated by poor contact of a plurality of temperature sensors applied to the skin of the patient.

Pre-Test Setting

Signal noise is quantified by measuring each rise and fall in temperature recorded by each temperature sensor 28A-28C, converting each negative change (i.e., each fall in temperature) into a positive number, and totaling all changes for each sensor. This method is then used to quantify the signal noise in previous tests which were evaluated to have acceptable or unacceptable levels of signal noise. This allows for the establishment of a signal noise threshold for each sensor 28A-28C. Tests which generate a signal noise level for any sensor which is higher than this threshold trigger a warning to the test operator that the test has generated a high level of noise, indicates which sensor is generating the signal noise (which should be addressed) and suggests that the temperature sensors are not making proper contact and that the overall test run should not be initiated until corrected, as well as re-applying or adjusting the EDR thermosensor 22 or CEDR thermosensor 122 against the skin.

Post-Test Setting

Assuming that the pre-test setting was satisfied and that the present invention 20/120A was activated to collect temperature sensor data, a post-test is conducted before the CSF flow status or flow rate is determined. This post-test check breaks the test into small time increments of multiple seconds (e.g., five seconds), establishes a straight line for each sensor reading from the temperature at the beginning of the time increment to the temperature at the end of the increment, computes the standard deviation of the actual signal vs the straight line, averages all the standard deviation in the test and compares the average standard deviation to an experimentally established threshold. Tests which generate a signal noise standard deviation average for any sensor which is higher than this threshold, trigger a warning to the test operator that the test has generated a high level of noise, indicates which temperature sensor 28A-28C is generating the signal noise (which should be addressed) and suggests that the test should be restarted or repeated.

Natural CSF Flow and Micro-Pumper Enhanced Flow

To address the long test time needed to assess natural flow and Micro-Pumper flow, a combined test procedure was developed. A timing diagram of this test procedure is shown in FIG. 16A. This procedure is implemented by the algorithm of the ShuntCheck software which instructs the operator as follows. This procedure begins with a natural flow assessment of a first ice placement and response measurement by a second ice placement (e.g., phases I and II) and a Micro-Pumper 300 procedure and a second response measurement (e.g., phases III-V). This procedure allows for an assessment of natural flow—the period prior to the placement of the Micro-Pumper 300—and an assessment of Micro-Pumper 300 flow—the period beginning with the Micro-Pumper placement.

The temperature signal for the Natural Flow period and for the total test are given, allowing the physician to quantify natural flow vs enhanced flow. A color coded time-temperature graphs is also provided, making test interpretation intuitive.

The combined natural and Micro-Pumper 300 test procedure begins with a natural flow assessment of 60 seconds ice placement and 120 seconds of response measurement. This is followed by a second 60 second ice placement, a 60 second Micro-Pumper 300 procedure and a 3 minute response measurement. This procedure allows for an assessment of natural flow—the period prior to the placement of the Micro-Pumper 300—and an assessment of Micro-Pumper 300 flow—the period beginning with the Micro-Pumper 300 placement.

The test result, shown in FIG. 16B (as an exemplary display screen), shows patient and test information, quantifies the temperature decrease during the Natural Flow phase of the test and the total temperature decrease during the test, reports Flow Confirmed or Flow Not Confirmed and provides the test operator notes on the left side of the results report and shows a time-temperature graph on the right side. This graph includes vertical blue bars which note the time periods when ice is applied and a vertical green bar which notes the time period of micro-pumping using the Micro-Pumper 300. The graph also includes a red-dashed line with shows the threshold temperature decrease required for a "Flow Confirmed" result. These graphical elements make graph interpretation easier and more intuitive.

Figure 17A:
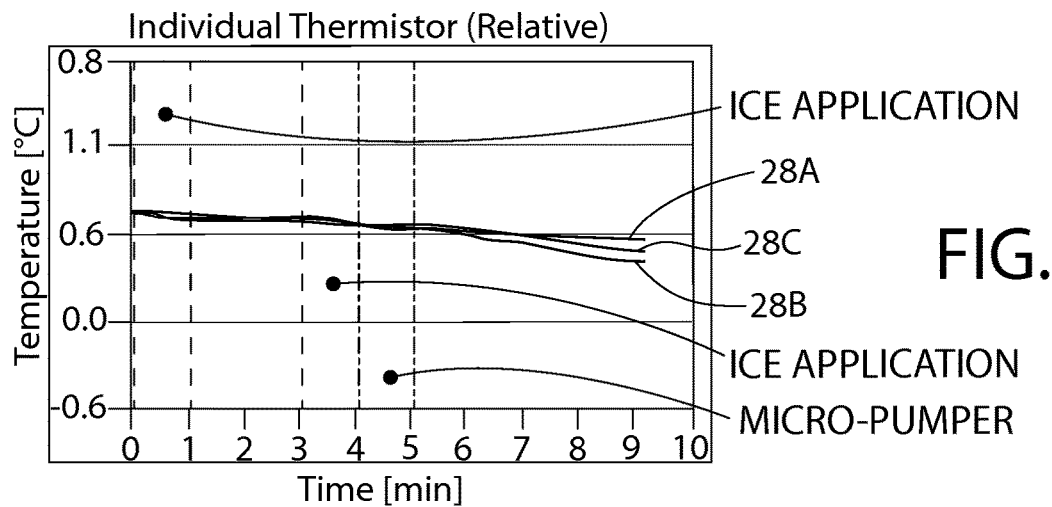
FIG. 17A is an exemplary display screen showing a patient's temperature sensor data indicating a no flow characteristic.
Figure 17B:
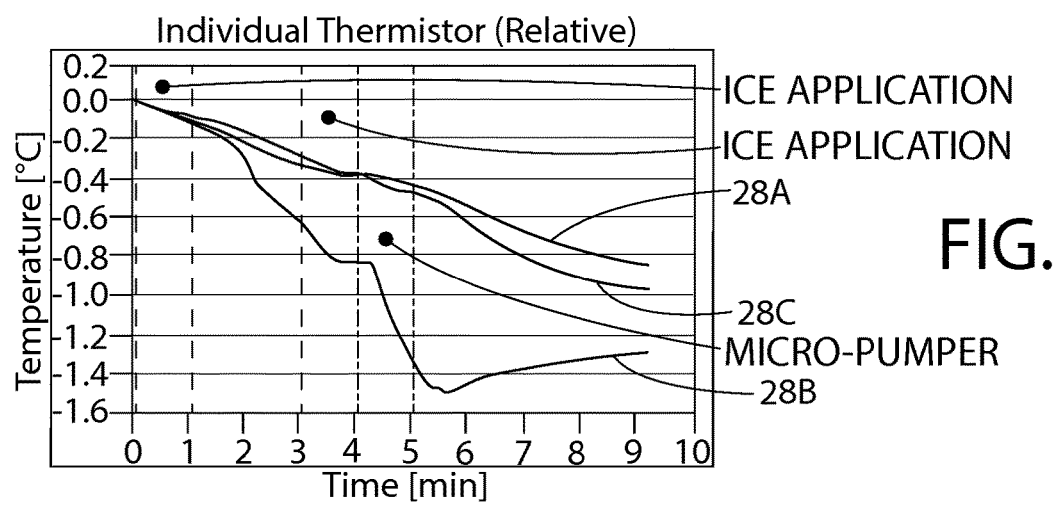
FIG. 17B is an exemplary display screen showing a patient's temperature sensor data indicating a CSF flow characteristic.

Flow Algorithm for Identifying Asymmetric Warming Response to Cold Source Placement In accordance with the previous discussion, cold source (e.g., ice pack) placement usually results in relatively uniform ambient cooling of the skin adjacent to the cooling source, including the skin under the temperature sensors 28A-28C. As a result, when there is no CSF flow through the shunt 13, the three temperature sensors 28A-28C register similar temperature readings as show in FIG. 17A. Conversely, when there is CSF flowing through the shunt 13, the test temperature sensor 28B indicates such by manifesting a greater temperature decrease due to the flow of the chilled CSF flow; this is clearly shown in FIG. 17B.

Figure 17C:
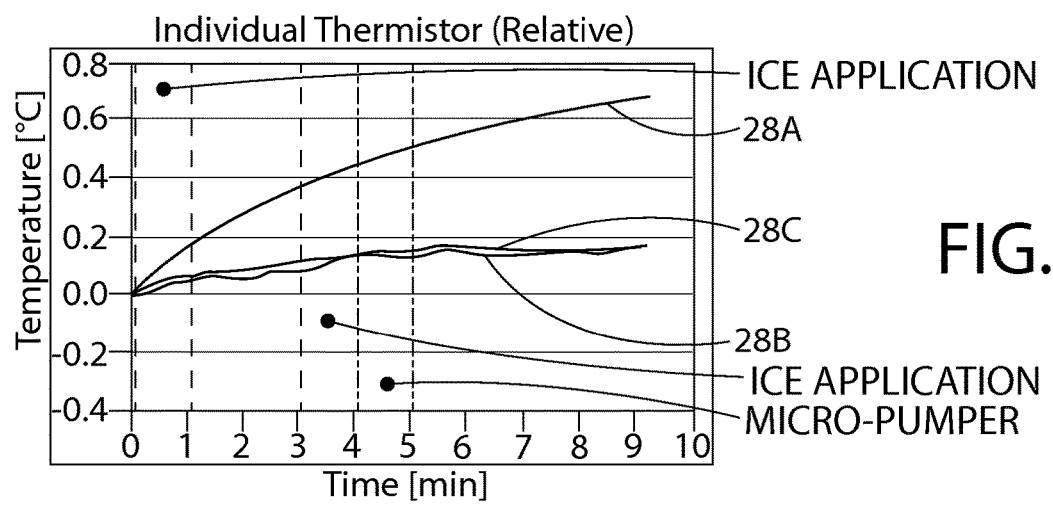
FIG. 17C is an exemplary display screen showing a patient's temperature sensor data that a ShuntCheck flow algorithm would alert an operator that a patient warming response was occurring and that the resultant temperature signal may not be accurate.

However, some patients exhibit non-uniform vasculature in their skin near the area of the thermosensor 22 (or 122) placement. As a result, these blood vessels may respond to the cold source placement and warm an area of the skin in a non-uniform manner. If this warming includes an area of skin covered by a control temperature sensor (e.g., 28A or 28C), the temperature sensors can indicate results similar to those shown in FIG. 17C, where the test temperature sensor 28B and one of the control temperature sensors (28A or 28C) track together, indicating a "no-CSF flow" condition, while the remaining control temperature sensor indicates a more pronounced temperature increase. In view of such a scenario, the differential temperature signal T1 −(T2+T3)/2 actually calculates a "CSF flow" condition, which is not correct.

Therefore, in order to alert an operator that such a patient "warming" response that may provide incorrect CSF flow data, a flow algorithm for identifying a warming response is provided. In particular, the ShuntCheck software monitors the parameters T1-T2 and T1-T3 to determine if either of these quanitites fails to exceed a predetermined threshold, an alert is provided to the operator that the differential temperature signal T1−(T2+T3)/2 may not be generating accurate CSF flow status/rate due to a patient "warming" response. Namely, Is T1-T2 or T1-T3<a threshold value?

If the answer is "yes", the ShuntCheck software continues to calculate the differential temperature signal but accompanied by an operator warning that such data is subject to a patient warming response. Furthermore, this threshold value would be >0° C. but it would need to be ≤the "flow confirmed" threshold (e.g., 0.2° C.) discussed previously.

An alternative, and less preferred alternative, to continue calculating the differential temperature signal T1−(T2+T3)/2 while issuing an operator warning about the patient warming response is to replace the differential temperature signal with the lesser of T1-T2 and T1-T3 during that patient warming response.

The present inventions 20 and 120 thus represent a new tool and clinical method for the diagnosis and early diagnosis of CSF shunt malfunction in hydrocephalus patients who arrive at the emergency department (ED) with symptoms consistent with shunt obstruction. Up to 30% of mortalities in shunted patients are attributed to shunt malfunction and there are currently no non-invasive techniques that can reliably be used as stand-alone diagnostic instruments for shunt obstruction. ShuntCheck rapidly determines (e.g., within 9 minutes) shunt patency. Its portability, ease of use, safety, and relative inexpensiveness enable it to be used routinely in EDs and in neurosurgical clinical settings.

There are currently 300,000 people in the U.S. with CSF shunts. Approximately 30,000 shunt revision surgeries are conducted annually in the U.S. Each year 120,000 patients present with symptoms of shunt failure to hospital emergency rooms—primarily to the 453 level I and II emergency rooms in the U.S. Strong sensitivity and specificity results demonstrated in a clinical study combined with the present invention's 20 non-invasive procedure can result in the ShuntCheck-thermo dilution method and ShuntCheck Micro-Pumper 300 combination becoming a standard of care for symptomatic hydrocephalus patients and enables neurosurgeons and emergency medicine physicians to reduce the number of CT Scans conducted on "false alarm" symptomatic patients and thereby reduce the radiation build-up caused by the scans.

While the invention has been described in detail and with reference to specific examples thereof, it will be apparent to one skilled in the art that various changes and modifications can be made therein without departing from the spirit and scope thereof.

What is claimed is:

1. An apparatus for evaluating cerebrospinal fluid (CSF) flow rate or flow status in a CSF shunt positioned under the skin of a patient, said apparatus comprising:
   a sensor pad comprising a flexible material configured for conforming to a patient's skin contour and having a body comprising a plurality of temperature sensors that are positioned transversely across said body at predetermined positions, said plurality of temperature sensors being aligned such that when said sensor pad is applied to the skin over the CSF shunt, one of said plurality of temperature sensors is positioned over the CSF shunt while the remaining plurality of temperature sensors are equally positioned on opposite sides of the CSF shunt; each of said temperature sensors configured to generate respective temperature data related to movement of a temperature pulse introduced into the CSF shunt from a cold source applied to the skin for a predetermined period, said body further comprising an alignment member that protrudes from an outside edge of said body, said alignment member acting as a guide for a user in positioning said cold source at a predetermined position upstream of said sensor pad;
   said sensor pad being disposable; and
   a sensor processing device that is electrically coupled to said sensor pad for receiving temperature data from each of said temperature sensors, said sensor processing device using said temperature data to determine a flow rate or flow status of said CSF through said shunt when said cold source is applied at said predetermined upstream position.

2. The apparatus of claim 1 wherein said sensor processing device determines said flow rate or flow status by taking a difference between said temperature data of said one of said plurality of temperature sensors that is positioned over the CSF shunt and an average of said temperature data of said remaining plurality of temperature sensors positioned on opposite sides of the CSF shunt, said difference being subsequently referred to as "temperature difference".

3. The apparatus of claim 2 wherein said sensor processing device adjusts said temperature difference based on the location of the CSF shunt below the skin surface by multiplying said temperature difference by a ratio of actual skin thickness over the CSF shunt to average skin thickness over the CSF shunt.

4. The apparatus of claim 3 wherein said sensor processing device determines a lowest point in said difference for determining a steady state of said temperature difference data.

5. The apparatus of claim 2 wherein said sensor processing device instructs an operator to conduct a test procedure for the determination of the CSF flow status or CSF flow rate by:
   applying the cold source against the patient's skin over the subcutaneously positioned CSF shunt for a first time period at predetermined upstream position, away from said pad, to transfer an initial cold pulse into said the CSF in said CSF shunt;
   displacing said cold source away from against the patient's skin over the subcutaneously positioned CSF shunt at said predetermined upstream position for a second time period so as not to cause discomfort to the patient by the application of the cold source for a prolonged period while said device receives temperature data from said plurality of temperature sensors based on said first cold pulse;
   re-applying said cold source a second time against the patient's skin over the subcutaneously positioned CSF shunt for a third time period at said predetermined upstream position; and
   removing said cold source from against the patient's skin over the subcutaneously positioned CSF shunt while said device again receives temperature data from said plurality of temperature sensors to determine the CSF flow status or CSF flow rate and thereby complete the test procedure.

6. The apparatus of claim 5 wherein the subcutaneously positioned CSF shunt comprises a valve positioned closely adjacent an outer skin surface of the patient and wherein said step of removing said cold source comprises externally applying a vibrating member to be in contact with said valve via the outer skin surface and activating said vibrating member to apply mechanical vibratory motion to said valve, for a fourth time period of time, such that physical reciprocation of said vibrating member causes said valve to reciprocate.

7. The apparatus of claim 1 wherein said sensor processing device alerts an operator, prior to running an evaluation of said CSF flow rate or CSF flow status, that said sensor pad comprising at least one of said plurality of temperature sensors is in partial or complete loss of contact with the skin of the patient, said alert being generated based on signal noise being detected in an output of at least one of said plurality of temperature sensors that exceeds a predetermined signal noise threshold during a pretest operation of said apparatus and if so to readjust positioning of said sensor pad against the patient's skin until outputs of said plurality of temperature sensors are below said predetermined signal noise threshold before running said evaluation of said CSF flow rate or CSF flow status, said pretest operation comprising the steps of:
- measuring each rise and fall in temperature detected by each one of said plurality of sensors;
- converting each fall in temperature, comprising a negative number, into a positive number for each one of said plurality of sensors;
- totaling all temperature changes for each one of plurality of sensors to form a total error for each sensor; and
- comparing said total error of each sensor to said predetermined signal noise threshold to determine if said total error exceeds said predetermined threshold or not and instructing an operator to re-apply said sensor pad to the skin and obtaining a new set of temperature data for all of said plurality of temperature sensors with said cold source applied if said predetermined threshold is exceeded.

8. The apparatus of claim 7 wherein said sensor processing device comprises a post-test setting mode in which said device alerts the operator that temperature data collected by at least one of said plurality of temperature sensors during said evaluation of CSF flow rate or CSF status exceeds a predetermined threshold for signal noise standard deviation and that said evaluation of CSF flow rate or CSF status should be repeated, said post-test setting mode comprising the steps of:
- separating temperature data collected from each one of said plurality of temperature sensors into time increments of multiple seconds;
- establishing a straight line for each one of said temperature data within each time increment;
- computing a standard deviation of an actual temperature signal with said straight line;
- averaging all of said standard deviations to form an average standard deviation;
- comparing said average standard deviation to an experimentally-established threshold; and
- activating a warning to the operator whenever said average standard deviation exceeds said experimentally-established threshold in order to have the operator re-collect temperature data from said plurality of temperature sensors by running said evaluation of said CSF flow rate or CSF flow status again.

9. The apparatus of claim 1 wherein said plurality of temperature sensors are coupled to a flex circuit secured to a first side of said body, said flex circuit configured to be in contact with the skin and configured to be applied to the skin, said flex circuit being conformable to the clavicle of the patient when said sensor pad is applied to the skin.

10. The apparatus of claim 9 wherein said plurality of temperature sensors comprises three temperature sensors and wherein said flex circuit comprises a long side segment from which projects three prongs, each comprising a respective one of said three temperature sensors and wherein said long side segment is transversely positioned across said body, said long side segment with said three prongs forming a configuration that minimizes a bulk of said flex circuit near said temperature sensors for reducing thermal conductivity and thermal crosstalk between said temperature sensors, thereby providing higher quality temperature signals.

11. The apparatus of claim 10 wherein said three temperature sensors are positioned 15 mm from each other.

12. The apparatus of claim 10 wherein said flex circuit comprises electric leads and wherein said electric leads are 4 mil wide, said 4 mil wide electrical leads reducing thermal conductivity while improving conformability.

13. The apparatus of claim 9 wherein said flex circuit is coupled to the body using a first adhesive layer applied to said first side.

14. The apparatus of claim 13 wherein a second adhesive layer is applied over said flex circuit, and wherein said second adhesive layer is in direct contact with said first adhesive layer, on said first side and wherein a release liner is applied over said second adhesive layer, said second adhesive layer forming a continuous adhesive layer configured for preventing each one of said plurality of temperature sensors from making contact with the skin of the patient.

15. The apparatus of claim 9 wherein said body comprises a second side, opposite said first side, and upon which alignment indicia is printed for directing the user to position said sensor pad correctly over the CSF shunt.

16. The apparatus of claim 1 wherein said pad comprises an outside edge and wherein a distance (SD) between said outside edge and said plurality of temperature sensors is defined as 16 mm<SD≤36 mm, said outside edge facing the cold source when said pad is placed in contact with the skin.

17. The apparatus of claim 16 wherein said distance (SD) is 28 mm.

18. The apparatus of claim 1 wherein said cold source comprises an area of at least 3 inches by 3 inches which provides a cold source footprint that permits said plurality of temperature sensors to detect a wider range of CSF shunt flows.

19. The apparatus of claim 1 wherein said sensor processing device further comprises an algorithm that:
- monitors a first difference between said temperature data of said one of said plurality of temperature sensors that is positioned over the CSF shunt and a first one of said remaining plurality of temperature sensors positioned on a left side of the CSF shunt;
- monitors a second difference between said temperature data of said one of said plurality of temperature sensors that is positioned over the CSF shunt and a second one of said remaining plurality of temperature sensors that is positioned on a right side of the CSF shunt opposite said first one of said remaining plurality of temperature sensors; and generates an alert if either one of said first or second differences fails to exceed a predetermined threshold.

20. The apparatus of claim 1 wherein said sensor processing device further comprises an algorithm that:
   monitors a first difference between said temperature data of said one of said plurality of temperature sensors that is positioned over the CSF shunt and a first one of said remaining plurality of temperature sensors positioned on a left side of the CSF shunt;
   monitors a second difference between said temperature data of said one of said plurality of temperature sensors that is positioned over the CSF shunt and a second of said remaining plurality of temperature sensors that is positioned on a right side of the CSF shunt opposite said first one of said remaining plurality of temperature sensors; and
   determines said flow rate or flow status based on said first or second difference, whichever is smaller in value.

21. An apparatus for measuring changes in skin temperature above a CSF shunt positioned under the skin of a patient, said apparatus comprising:
   a sensor pad having a body comprising a plurality of temperature sensors that are positioned transversely across said body at predetermined positions, said plurality of temperature sensors being aligned such that when said sensor pad is applied to the skin over the CSF shunt, one of said plurality of temperature sensors is positioned over the CSF shunt while the remaining plurality of temperature sensors are equally positioned on opposite sides of the CSF shunt; each of said temperature sensors configured to generate respective temperature data related to movement of a temperature pulse introduced into the CSF shunt from a cold source, of a size larger than said pad, applied to the skin for a predetermined period; said body further comprising an alignment member that protrudes from an edge of said pad, said alignment member acting as a guide for a user in positioning said cold source adjacent said pad and against the skin of the patient to maintain said cold source at a predetermined upstream position away from said plurality of temperature sensors over the CSF shunt, wherein said sensor pad is disposable; and
   a sensor processing device that is electrically coupled to said sensor pad for receiving temperature data from each of said temperature sensors, said sensor processing device comprising an algorithm for taking a difference between said temperature data of said one of said plurality of temperature sensors that is positioned over the CSF shunt and an average of said temperature data of said remaining plurality of temperature sensors positioned on opposite sides of the CSF shunt, said algorithm adjusting said difference between said temperature data based on the location of the CSF shunt below the skin surface by multiplying said temperature difference by a ratio of actual skin thickness to average skin thickness.

* * * * *